US011746070B2

(12) United States Patent
Wang et al.

(10) Patent No.: US 11,746,070 B2
(45) Date of Patent: Sep. 5, 2023

(54) CONVERSION OF PARAFFINS TO OLEFINS AND HEAVIER HYDROCARBONS MEDIATED BY METAL OXIDES

(71) Applicant: ExxonMobil Technology and Engineering Company, Annandale, NJ (US)

(72) Inventors: Kun Wang, Bridgewater, NJ (US); Jonathan E. Mitchell, Easton, PA (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 165 days.

(21) Appl. No.: 16/693,633

(22) Filed: Nov. 25, 2019

(65) Prior Publication Data

US 2020/0199042 A1 Jun. 25, 2020

Related U.S. Application Data

(60) Provisional application No. 62/783,530, filed on Dec. 21, 2018.

(51) Int. Cl.
  *C07C 5/333* (2006.01)
  *C07C 5/42* (2006.01)
  *C10G 11/04* (2006.01)

(52) U.S. Cl.
  CPC ............ *C07C 5/3332* (2013.01); *C10G 11/04* (2013.01); *C07C 2523/72* (2013.01);
  (Continued)

(58) Field of Classification Search
  CPC ..... C07C 5/3332; C07C 5/41; C07C 2523/72; C07C 2523/75; C07C 2523/40;
  (Continued)

(56) References Cited

U.S. PATENT DOCUMENTS 3,617,492 A    11/1971   Lorenz et al.
3,719,721 A *   3/1973   Hansford ................ C07C 5/322
                                              585/420

(Continued)

FOREIGN PATENT DOCUMENTS

CN       108410498 A      8/2018
EP         0403462 B1 *   12/1996  ............. B01J 23/22

OTHER PUBLICATIONS

Tijani, M.M, "Synthesis and study of metal-based oxygen carriers (Cu, Co, Fe, Ni) and their interaction with supported metal oxides (Al2O3, CeO2, TiO2, ZrO2) in a chemical looping combustion system", Energy, 2017, 138, 873-882.

(Continued)

*Primary Examiner* — In Suk C Bullock
*Assistant Examiner* — Jason Y Chong
(74) *Attorney, Agent, or Firm* — Shook, Hardy & Bacon L.L.P.

(57) ABSTRACT

The present disclosure provides processes to convert paraffins to corresponding olefins and or heavier hydrocarbons. In at least one embodiment, a process includes introducing, at a temperature of from about 50° C. to about 500° C., a hydrocarbon feed comprising paraffins to a first metal oxide comprising one or more group 1 to group 17 metal and one or more oxygen. The process includes obtaining a product mixture comprising one or more C3-C50 cyclic olefins, one or more C2-C50 acyclic olefins, one or more C5-C200 hydrocarbons, such as one or more C5-C100 hydrocarbons, or a mixture thereof. In at least one embodiment, the product mixture is substantially free of H2 (e.g., <500 ppm). The introducing can reduce the first metal oxide to form a second metal oxide. Processes may include introducing the second metal oxide to an oxidizing agent to form the first metal oxide.

25 Claims, 6 Drawing Sheets

(52) U.S. Cl.
CPC .............. *C10G 2300/1044* (2013.01); *C10G 2300/1081* (2013.01); *C10G 2400/20* (2013.01); *C10G 2400/22* (2013.01)

(58) Field of Classification Search
CPC .......... C07C 2523/06; C07C 2523/745; C07C 2523/755; C07C 2523/02; C07C 2523/04; C10G 11/04; C10G 2300/1044; C10G 2300/1081; C10G 2400/20; C10G 2400/22
See application file for complete search history.

(56) References Cited

U.S. PATENT DOCUMENTS

| | | | | |
|---|---|---|---|---|
| 5,430,209 | A | * | 7/1995 | Agaskar .................... C07C 5/42 585/315 |
| 8,435,920 | B2 | | 7/2013 | White et al. |
| 9,688,626 | B2 | | 6/2017 | Wang et al. |
| 2016/0318828 | A1 | * | 11/2016 | Washburn ............. C07C 5/3337 |
| 2018/0297914 | A1 | * | 10/2018 | Aljundi ................ B01J 37/0009 |

OTHER PUBLICATIONS

Neal et al., "Redox Catalysts for Partial Oxidation of Light Paraffins Under a Chemical-Looping Scheme", Prepr. Pap.-Am. Chem. Soc., Div. Energy Fuels 2015, vol. 60 (2), pp. 172-173.

Oviol et al.,"Mind the gap", Hydrocarbon Engineering, Sep. 2012, p. 1-4.

* cited by examiner

CONVERSION OF PARAFFINS TO OLEFINS AND HEAVIER HYDROCARBONS MEDIATED BY METAL OXIDES

CROSS-REFERENCE TO RELATED APPLICATION

This application claims the benefit of U.S. Provisional Application No. 62/783,530 filed on Dec. 21, 2018, the entire contents of which is incorporated herein by reference.

FIELD

The present disclosure provides processes to convert naphtha range hydrocarbons to olefins and distillates. The present disclosure further provides compositions including distillates.

BACKGROUND

As the production of shale and tight oils is increasing in the United States of America, light paraffins (e.g., C3 to C9), such as Liquefied Petroleum Gas ("LPG"), Natural Gas Liquids ("NGL"), are becoming increasingly abundant and at lower costs. Ethane to light naphtha range paraffins are largely fed to steam crackers or dehydrogenated to make olefins. For example, ethane is steam-cracked to make ethylene, and light naphtha (b.p. 15.5° C.-71° C.) is steam cracked to make ethylene, propylene, and small volumes of dienes.

Short-chain alkanes (e.g., C2-alkanes to C5-alkanes) can also be converted to their corresponding olefin using dehydrogenation technologies. Dehydrogenation of short-chain alkanes (e.g., C2 to C5) commonly uses one of two types of catalysts: platinum-based catalyst(s) or chromium oxide catalyst(s). The dehydrogenation process is typically carried out at temperatures >450° C., and under ambient or sub-ambient pressure, mainly due to the fact that paraffin dehydrogenation to olefins, or dehydrogenative coupling to heavier paraffins, are both thermodynamically unfavored and conversion is equilibrium limited. Hence, the free energy of the dehydrogenation reaction only becomes favorable at temperatures of at least 600° C. To manage the frequency of a catalyst regeneration process due to coking, reactors such as moving-bed, cyclic swing-bed, or fluidized bed reactors are employed. On the other hand, heavy naphtha (b.p. 71° C.-182° C.) is typically fed to catalytic reformers in order to produce aromatics and hydrogen, but no catalyst/process that selectively dehydrogenates naphthenes to mono-olefins has been described.

Conversion of light paraffins to distillate is typically performed using the following technologies: 1) steam cracking or catalytic dehydrogenation of paraffins to generate olefins, followed by olefin oligomerization; 2) converting the feed to syngas via partial oxidation, followed by Fischer-Tropsch or methanol to hydrocarbons synthesis. However, these approaches involve high temperatures (e.g. >400° C.) and are energy intensive.

As the reformers reach capacity, coupled with the limited growth in demand for aromatics, there is a continuous need to convert heavy naphtha, particularly heavy virgin naphtha (HVN), to large volume, higher value products. Furthermore, global transportation fuels outlook suggests that the long-term demand for automotive gas (e.g., gasoline) will decrease, while the demand for octane is expected to grow with the increasing use of high-compression engines. Conversely, global fast growing demands for distillate (e.g., jet, diesel) favors the conversion of heavy naphtha (low-octane gasoline; e.g., Research Octane Number ("RON") and Motor Octane Number ("MON") for cyclohexane are 83.0 and 77.2, respectively; RON and MON for n-heptane are zero) to distillate range liquids.

Furthermore, the excess in supply of light alkanes and olefins due to shale gas and hydraulic fracturing (also referred to as "fracking"), in addition to traditional light cuts (e.g., C5 of the Fluid Catalytic Cracking, "FCC"), has limited new uses. Hence, growing the molecular weight of light alkanes and olefins into fuel/lubricant ranges would be valuable, particularly due to the lower value of light alkanes, and the higher value of fuels, and lubricant range hydrocarbons.

Metal oxide materials have found use as oxygen carriers for catalytic upgrading of chemical species via cyclic catalytic conversion, or chemical looping combustion of natural gas and methane, especially for the production of syngas. Accordingly, metal oxides and mixed metal oxides have wide applications, such as catalyst, adsorbents, superconductors, semiconductors, ceramics, antifungal agents. Despite the energy saving role of such process, high temperatures are still required (e.g. about 700° C. to about 900° C.), and often need additional solvent in the feed. These processes often require the use of metal oxides, such as CrOx and Ga2O3, as catalysts for paraffin dehydrogenation where H2 is present (either as co-feed or product) in those systems which produces a high content of hydrogen in the dehydrogenated products.

Therefore, there remains a need for processes that provide a highly efficient and economical conversion of heavy hydrocarbons to light distillates and or mid-distillates, and or as distillate range liquids, under mild conditions. Furthermore, there is a need for processes to convert heavy naphtha, particularly naphthene-rich heavy virgin naphtha, to distillate range products.

SUMMARY

The present disclosure provides processes to convert paraffins to corresponding olefins and or heavier hydrocarbons under mild conditions (e.g., low temperature ≤400° C.) using metal oxides (reagents, also referred to as "reactants"). Processes of the present disclosure may include upgrading a hydrocarbon feed. In at least one embodiment, a process includes introducing, at a temperature of from about 50° C. to about 500° C., a hydrocarbon feed comprising paraffins to a first metal oxide comprising one or more group 1 to group 17 metal and one or more oxygen. The process includes obtaining a product mixture including one or more C3-C50 cyclic olefin, one or more C2-C50 acyclic olefin, one or more C5-C200 hydrocarbon, such as one or more C5-C100 hydrocarbon, or a mixture thereof. In at least one embodiment, the product mixture is substantially free of H2 (e.g., <500 ppm, such as <10 ppm, such as <5 ppm). The introducing process can reduce the first metal oxide to form a second metal oxide (a reduced metal oxide). Processes may include introducing the second metal oxide to an oxidizing agent to form the first metal oxide.

Commercially valuable products such as ethylene and propylene can be formed using processes of the present disclosure.

DETAILED DESCRIPTION

Figure 1:
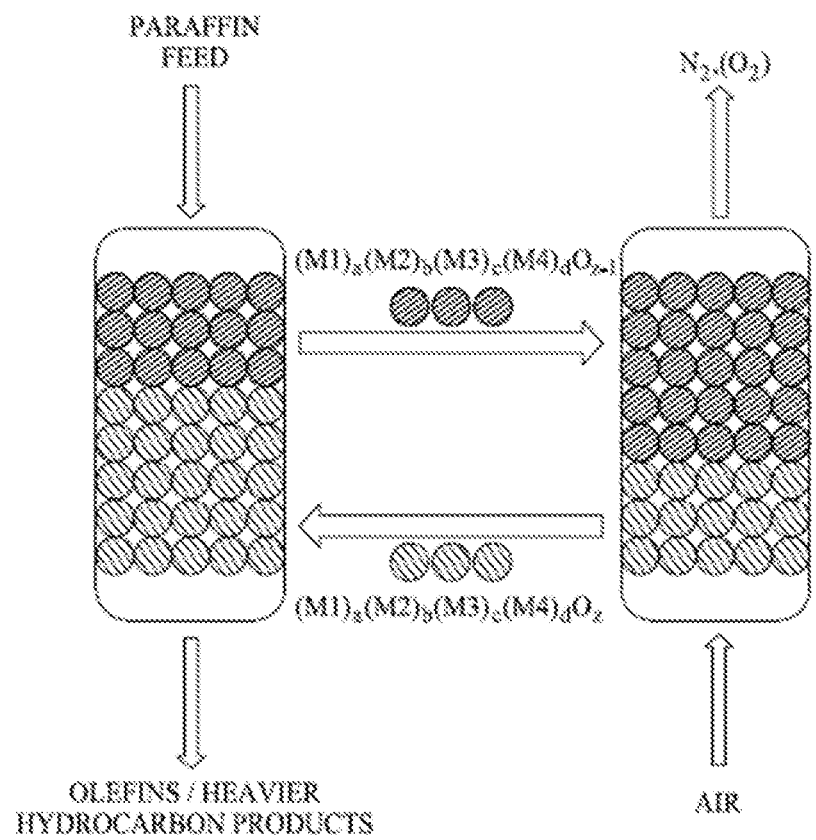
FIG. 1 is a schematic diagram of a chemical looping process in which a first metal oxide is reduced into a second metal oxide that is oxidized via an oxidizing agent to form the first metal oxide, and a paraffin feed is converted via dehydrogenation to a corresponding olefin and or converted via dehydrogenative coupling to heavier hydrocarbon products, according to one embodiment.

The present disclosure provides processes to convert paraffins to corresponding olefins and or heavier hydrocarbons under mild conditions (e.g., low temperature ≤400° C.) using metal oxides. Furthermore, the present disclosure provides a process for upgrading a hydrocarbon feed, the process including: 1) introducing, at a temperature of from about 50 C to about 500° C., a hydrocarbon feed comprising paraffins to a catalytic reduction unit and a first metal oxide comprising one or more group 1 to group 17 metal and one or more oxygen; ii) and obtaining a product mixture including one or more C3-C50 cyclic olefin, one or more C2-C50 acyclic olefin, one or more C5-C200 hydrocarbon, such as one or more C5-C100 heavier hydrocarbon, or a mixture thereof. Commercially valuable products, such as ethylene and propylene, can be formed using processes of the present disclosure.

As used herein, and unless otherwise indicated, a "metal oxide" refers to a metal oxide reagent/reactant that is reduced during a dehydrogenation process of the present disclosure. In comparison, a metal oxide catalyst would be regenerated to its original form (e.g. oxidation state) during a chemical reaction. Metal oxide reagents/reactants of the present disclosure can be regenerated from their reduced forms by treating the reduced form of the metal oxide to an oxidizing agent, as described in more detail below.

Dehydrogenation can reduce the first metal oxide to form a second metal oxide, also referred to as "a reduced metal oxide". Methods may include: i) introducing the reduced metal oxide to a catalytic oxidation unit; ii) and regenerating the first metal oxide in the catalytic oxidation unit by contacting the second metal oxide with an oxidizing agent (e.g., air).

In at least one embodiment, the conversion of paraffins (e.g., isoparaffins, normal-paraffins, neoparaffins, cyclic paraffins, or mixtures thereof) to one or more C3-C50 cyclic olefins, one or more C2-C50 acyclic olefins, one or more C5-C200 hydrocarbons, such as one or more C5-C100 hydrocarbons, or a mixture thereof (and the product mixture is substantially free of H2 (e.g., <10 ppm, such as <5 ppm), is performed using a metal oxide, also referred to as metal oxide, is represented by Formula (I):

$$(M1)_a(M2)_b(M3)_c(M4)_dO_z \qquad (I)$$

wherein:
M1 is a group 1, 2, 3, 4, 5, 6, 7, 8, 9, 10, 11, 12, 13, 14, 15, 16, or 17 metal;
M2 is a group 1, 2, 3, 4, 5, 6, 7, 8, 9, 10, 11, 12, 13, 14, 15, 16, or 17 metal;
M3 is a group 1, 2, 3, 4, 5, 6, 7, 8, 9, 10, 11, 12, 13, 14, 15, 16, or 17 metal;
M4 is a group 1, 2, 3, 4, 5, 6, 7, 8, 9, 10, 11, 12, 13, 14, 15, 16, or 17 metal;
a is 0.01≤a≤4;
b is 0≤b≤4;
c is 0≤c≤4;
d is 0≤d≤4; and
z is 1≤z≤12.

In an alternate embodiment, b, c, d of Formula (I) is 0 and the metal oxide is represented by Formula (II):

$$(M1)_aO_z \qquad (II)$$

wherein:
M1 is a group 1, 2, 3, 4, 5, 6, 7, 8, 9, 10, 11, 12, 13, 14, 15, 16, or 17 metal;
a is 0.01≤x≤4; and
z is 1≤z≤12.

Processes of the present disclosure may provide the following advantages: 1) reduction of the metal oxides can provide significant driving force to overcome thermodynamic limitations for paraffin conversions to olefins or heavier hydrocarbons, thus the reaction can be performed at significantly lower temperatures (e.g., <400° C.) than conventional approaches (e.g., steam cracking or dehydrogenation), resulting in reduction of greenhouse gas (GHG) emissions; 2) high selectivity for the formation of monoolefins, such as cyclic olefins, can be obtained (such as a selectivity of 50% or greater), thus reducing or eliminating the formation of aromatics (e.g., benzene); 3) little or no direct contact of O2 with hydrocarbons, thus avoiding undesired reactions of free O2 with radical species that lead to over oxidation and improving selectivity vs. direct oxidation; 4) pure O2 is not needed as the reduced metal oxides (M1)a(M2)b(M3)c(M4)dOz-1, such as (M1)aOz-1, can be oxidized by air oxidation to form the first metal oxide (M1)a(M2)b(M3)c(M4)dOz, such as (M1)aOz. Olefins generated from a process of the present disclosure can be isolated as chemical intermediates, polymerized (e.g., oligomerized) to chemicals, fluids, or distillate products. For example, olefins generated from a process of the present disclosure can be used as monomers for polymers production (e.g., polyolefins production via metathesis).

All numerical values within the detailed description and the claims herein are modified by "about" or "approximately" the indicated value, and take into account experimental error and variations that would be expected by a person of ordinary skill in the art.

For purposes herein, the numbering scheme for the Periodic Table Groups is used as described in Chemical and Engineering News, 63(5), pg. 27 (1985). For example, a "Group 4 metal" is an element from Group 4 of the Periodic Table, e.g., Hf, Ti, or Zr.

Unless otherwise indicated, room temperature is 23° C.

As used herein, and unless otherwise specified, the term "Cn" means hydrocarbon(s) having n carbon atom(s) per molecule, wherein n is a positive integer. As used herein, and unless otherwise specified, the term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and or unsaturated), including mixtures of hydrocarbon compounds having different values of n. Additionally, the hydrocarbon compound may contain, for example, heteroatoms such as sulphur, oxygen, nitrogen, or any combination thereof.

A "polymer" has two or more of the same or different monomer ("mer") units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers.

As used herein, the term "base stock" means a hydrocarbon liquid useable as a major component of a lubricating oil. As used herein, the term "base oil" refers to a blend of base stocks useable as a major component of a lubricating oil. As used herein, the term "major component" means a component present in a lubricating oil in an amount of about 50 weight percent (wt %) or greater. As used herein, the term "minor component" means a component (e.g., one or more lubricating oil additives) present in a lubricating oil in an amount less than about 50 wt %.

The term "continuous" means a system that operates without interruption or cessation. For example a continuous process to produce an olefin and or a hydrocarbon product would be one where the reactants are continually introduced into one or more reactors and the olefin and or the hydrocarbon product can be continually withdrawn during a conversion process (e.g., dehydrogenation process; dehydrogenative coupling).

For purposes of this disclosure and claims thereto, the term "substituted" means that a hydrogen atom in the compound or group in question has been replaced with a group or atom other than hydrogen. The replacing group or atom is called a substituent. Substituents can be, e.g., a substituted or unsubstituted hydrocarbyl group, a heteroatom, and the like. For example, a "substituted hydrocarbyl" is a group made of carbon and hydrogen where at least one hydrogen therein is replaced by a non-hydrogen atom or group. A heteroatom can be nitrogen, sulfur, oxygen, halogen, etc.

The term "alkenyl" means a straight-chain, branched-chain, or cyclic hydrocarbon radical having one or more double bonds. These alkenyl radicals may be optionally substituted. Examples of suitable alkenyl radicals can include ethenyl, propenyl, allyl, 1,4-butadienyl cyclopropenyl, cyclobutenyl, cyclopentenyl, cyclohexenyl, cyclooctenyl, and the like, including their substituted analogues.

The term "alkoxy" or "alkoxide" means an alkyl ether or aryl ether radical where the term alkyl is as defined above. Examples of suitable alkyl ether radicals can include methoxy, ethoxy, n-propoxy, iso-propoxy, n-butoxy, iso-butoxy, sec-butoxy, tert-butoxy, phenoxyl, and the like.

The term "aryl" or "aryl group" means a six carbon aromatic ring and the substituted variants thereof, such as phenyl, 2-methyl-phenyl, xylyl, 4-bromo-xylyl. Likewise, heteroaryl means an aryl group where a ring carbon atom (or two or three ring carbon atoms) has been replaced with a heteroatom, such as N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

Reference to an alkyl, alkenyl, alkoxide, or aryl group without specifying a particular isomer (e.g., butyl) expressly discloses all isomers (e.g., n-butyl, iso-butyl, sec-butyl, and tert-butyl).

For purposes of the present disclosure, "alkoxides" include those where the alkyl group is a C1 to C10 hydrocarbyl. The alkyl group may be straight chain, branched, or cyclic. The alkyl group may be saturated or unsaturated. In at least one embodiment, the alkyl group may include at least one aromatic group.

The terms "hydrocarbyl radical," "hydrocarbyl," and "hydrocarbyl group," are used interchangeably. Likewise, the terms "group," "radical," and "substituent" are also used interchangeably. For purposes of this disclosure, "hydrocarbyl radical" is defined to be C1 to C100 radicals, that may be linear, branched, or cyclic, and when cyclic, aromatic or non-aromatic. Examples of such radicals can include methyl, ethyl, n-propyl, isopropyl, n-butyl, isobutyl, sec-butyl, tert-butyl, pentyl, iso-amyl, hexyl, octyl, cyclopropyl, cyclobutyl, cyclopentyl, cyclohexyl, cyclooctyl, and the like including their substituted analogues.

The term "aralkyl" means a univalent radical derived from an alkyl radical by replacing one or more hydrogen atoms by one or more aryl groups.

The term "alkaryl" means an aryl-substituted alkyl radical (e.g., propyl-phenyl), such as a radical in which an aryl group is substituted for a hydrogen atom of an alkyl group.

The term "alkynyl" (also referred to as "ynyl") means a univalent aliphatic hydrocarbon radical derived from an alkyne.

The term "ring atom" means an atom that is part of a cyclic ring structure. By this definition, a benzyl group has six ring atoms and tetrahydrofuran has 5 ring atoms.

A heterocyclic ring is a ring having a heteroatom in the ring structure as opposed to a heteroatom substituted ring where a hydrogen on a ring atom is replaced with a heteroatom. For example, tetrahydrofuran is a heterocyclic ring and 4-N,N-dimethylamino-phenyl is a heteroatom-substituted ring.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic.

The term "alpha-olefin" refers to an olefin having a terminal carbon-to-carbon double bond in the structure thereof ((RaRb)—C═CH2, where Ra and Rb can be independently hydrogen or any hydrocarbyl group; such as Ra is hydrogen and Rb is an alkyl group). A "linear alpha-olefin" is an alpha-olefin defined in this paragraph wherein Ra is hydrogen, and Rb is hydrogen or a linear alkyl group.

For the purposes of the present disclosure, ethylene shall be considered an alpha-olefin.

The term "vinyl" means an olefin having the following formula:

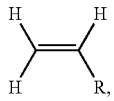

wherein R is a hydrocarbyl group, such as a saturated hydrocarbyl group.

The term "vinylidene" means an olefin having the following formula:

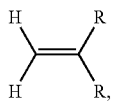

wherein each instance of R is independently a hydrocarbyl group, such as a saturated hydrocarbyl group.

The term "vinylene" or "1,2-di-substituted vinylene" means
(i) an olefin having the following formula (which is a "cis-" conformation):

or
(ii) an olefin having the following formula (which is a "trans-" conformation):

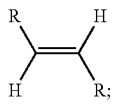

or
(iii) a mixture of (i) and (ii) at any proportion thereof, wherein each instance of R is independently a hydrocarbyl group, such as saturated hydrocarbyl group.

The term "internal olefin" includes olefins that are vinylenes.

The term "tri-substituted vinylene" means an olefin having the following formula:

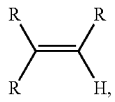

wherein each instance of R is independently a hydrocarbyl group, such as a saturated hydrocarbyl group.

An internal olefin (e.g., monomers) of the present disclosure can be a linear or branched C4-C50 olefin having one or more carbon-carbon double bonds along the olefin backbone (also referred to as "internal unsaturation") instead of, or in addition to, a carbon-carbon double bond at a terminus of the olefin (also referred to as "terminal unsaturation"). Linear or branched C4-C50 internal olefins may be referred to as C4-C50 internal-olefins. In addition to internal unsaturations, a C4-C50 internal olefin may additionally have one or more terminal unsaturations. An internal olefin can have one or more cis-conformations or one or more trans-conformations.

In at least one embodiment, an internal olefin is selected from a cis-configuration, trans-configuration, or mixture thereof of one or more of 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, and 5-decene. Internal olefins of the present disclosure can be obtained from commercial sources (such as Sigma Aldrich or TCI) and/or may be obtained from refined hydrocarbon feeds such as fluid catalytic cracking (FCC) gasoline or coker naphtha.

Dehydrogenation and Dehydrogenative Coupling Processes and the Metal Oxide Regeneration Process The present disclosure provides processes for converting a hydrocarbon feedstock (e.g., heavy naphtha, biomass, light paraffins, etc.) or a mix of two or more hydrocarbon feedstocks, comprising contacting the feedstock with one or more metal oxide $(M1)_a(M2)_b(M3)_c(M4)_dO_z$ (I) and or one or more metal oxide $(M1)_aO_z$ (II), and further obtaining a product mixture including one or more C3-C50 cyclic olefin, one or more C2-C50 acyclic olefin, one or more C5-C200 hydrocarbon, such as one or more C5-C100 hydrocarbon, or a mixture thereof. In at least one embodiment, the product mixture is substantially free of H2 (e.g., <500 ppm, such as <100 ppm, such as <10 ppm, such as <5 ppm, such as <1 ppm). The hydrocarbon feedstock can be one or more C3-C50 cyclic alkanes, one or more C2-C50 acyclic alkanes (e.g., iso-, linear, normal, and or branched (substituted) alkanes).

Processes of the present disclosure may be performed via a cyclic process (chemical looping or pulsed feed) based on a circulating fluidized bed process and system, or a switched (between air and the hydrocarbon feedstock) feed fluidized bed system, or switched feed fixed bed system, in which air and the hydrocarbon feedstock are alternated. Fine droplets or vapor of the hydrocarbon feedstock and air can be introduced over the metal oxide bed along with the oxygen carrier (e.g., metal oxide (I) and or metal oxide (II)), for example.

A process can be operated in a cyclic mode without moving the solids, thus by cycling through a paraffin conversion process and an oxide regeneration process (e.g., in a reverse-flow reactor), or in a continuous fashion (as shown in FIG. 1) by moving the solids through the paraffin conversion unit and oxide regeneration unit (e.g., moving solid beds, fluidized beds). Alternatively, the metal oxide can be shaped into one or more membrane reactor(s), planar or tubular, providing continuous operations with paraffin conversion and metal oxide regeneration, which can occur on separate sides of the membrane.

In addition to the reactivity toward paraffins and the capability to regenerate the first metal oxide (by oxidizing the second metal oxide (also referred to as "spent material" or "reduced material")) via air flow, the active oxygen content, also referred to as the "oxygen capacity", can be another important parameter in selecting the metal oxides. The oxygen capacity of the metal oxides will be discussed further.

Processes may include: i) contacting a first metal oxide (e.g., metal oxide (M1) a(M2)b(M3)c(M4)dOz (I) and or metal oxide (M1)aOz (II)) with a reducing substance (e.g., paraffins); ii) reducing the metal oxide, such as metal oxide (M1)a(M2)b(M3)c(M4)dOz (I) and or metal oxide (M1)aOz (II), with the reducing substance (e.g., paraffins) to a reduced metal oxide (M1)a(M2)b(M3)c(M4)dOz-1 and or (M1)aOz-1, respectively; and iii) regenerating the first metal oxide (e.g., (M1)a(M2)b(M3)c(M4)dOz and or (M1)aOz) using an oxidizing agent (e.g., air) at a partial pressure of about 1 psig to about 100 psig (e.g., metal oxide (I) and or metal oxide (II)).

The reducing substance (e.g., paraffins) can be one or more gas, liquid, or solid substance, or a mixture thereof. For example, when the reducing substance (e.g., paraffins) is gas, the reducing substance may be introduced to the catalytic reduction unit at a partial pressure of from about 15 psig to about 2000 psig, such as from about 15 psig to about 1,000 psig, such as from about 15 psig to about 200 psig. In at least one embodiment, contacting the metal oxide (M1)a(M2)b(M3)c(M4)dOz (I) and or the metal oxide (M1)aOz (II) includes cyclically exposing a fixed bed containing the metal oxide (M1)a(M2)b(M3)c(M4)dOz (I) and or the metal oxide (M1)aOz (II) to the reducing substance (e.g., paraffins) and to the oxidizing gas (e.g., air). In an alternate embodiment, contacting the metal oxide (M1)a(M2)b(M3)c(M4)dOz (I) and or the metal oxide (M1)aOz (II) includes cyclically exposing the fixed bed containing the metal oxide (M1)a(M2)b(M3)c(M4)dOz (I) and or the metal oxide (M1)aOz (II) to a continuous feed of the oxidizing gas (e.g., air) and intermittently feeding the reducing substance (e.g., paraffins). In another alternative embodiment, contacting the metal oxide (M1)a(M2)b(M3)c(M4)dOz (I) and or the metal oxide (M1)aOz (II) includes cyclically exposing the fixed bed containing the metal oxide (M1)a(M2)b(M3)c(M4)dOz (I) and or the metal oxide (M1)aOz (II) to a continuous feed of the reducing substance (e.g., paraffins) and intermittently feeding the oxidizing gas (e.g., air).

Furthermore, contacting the metal oxide (M1)a(M2)b(M3)c(M4)dOz (I) and or the metal oxide (M1)aOz (II) may include: i) circulating the metal oxide (M1)a(M2)b(M3)c(M4)dOz (I) and or the metal oxide (M1)aOz (II) in a fluidized bed system during the cyclic contacting of the metal oxide (I) and or (II), with a reducing substance (e.g., paraffins); ii) introducing the second metal oxide (M1)a(M2)b(M3)c(M4)dOz-1 and or (M1)aOz-1, to an oxidizing agent (e.g., oxidizing gas, such as air). Contacting the metal oxide (M1)a(M2)b(M3)c(M4)dOz (I) and or the metal oxide (M1)aOz (II) may also include circulating the metal oxide(s) in a fluidized bed system wherein the metal oxide(s) (I) and or (II) can be reduced in a reactor and can be circulated to a regeneration unit for contacting the second metal oxide (also referred to as the reduced metal oxide(s) (M1)a(M2)b(M3)c(M4)dOz-1 and or (M1)aOz-1) with the oxidizing gas (e.g., air).

In at least one embodiment, the process includes separating the C3-C50 cyclic olefins, C2-C50 acyclic olefins, and or C5-C200 hydrocarbon products, such as C5-C100 heavier hydrocarbon products via distillation.

Accordingly, the present disclosure can provide a process for a cyclic catalytic partial oxidation of a hydrocarbon feedstock which may include: (i) as an oxidation process, passing air over one or more second metal oxide(s) (e.g., (M1)a(M2)b(M3)c(M4)dOz-1 and or (M1)aOz-1) comprising a metal or metal oxide that can be configured to capture oxygen from the air to produce an oxidized metal oxide, such as (I) and or (II), and producing an effluent including oxygen-reduced air; (ii) passing the hydrocarbon feedstock over the oxidized metal oxide(s), such as (I) and or (II), in a reduction process to create a product gas comprising olefins and or heavier hydrocarbons, wherein the oxidized metal oxide(s), such as (I) and or (II), can become reduced or partially reduced, thus creating a second metal oxide (e.g., (M1)a(M2)b(M3)c(M4)dOz-1 and or (M1)aOz-1); and (iii) repeating (i) to oxidize the reduced metal oxide(s) (e.g., (M1)a(M2)b(M3)c(M4)dOz-1 and or (M1)aOz-1). For example, air can be passed continuously over the oxygen carrying (or oxygen storing) metal oxide(s) (e.g., (M1)a(M2)b(M3)c(M4)dOz-1 and or (M1)aOz-1), and pulses of hydrocarbon feedstock can be delivered periodically, by co-feeding with the air flow. In a cyclic (chemical looping or pulsed feed) mode, fine droplets or vapor of the hydrocarbon feedstock and air can be introduced over the oxygen carrying bed along with an oxygen carrying (or oxygen storing) metal oxide(s) (e.g., (M1)a(M2)b(M3)c(M4)dOz-1 and or (M1)aOz-1). The feed to the bed can be switched between this mixture and air (or other oxidant). Alternatively, air can be fed continuously to the bed and the hydrocarbon feed (such as a liquid hydrocarbon feed) can be delivered to the reactor (as droplets or vapor, for example).

The hydrocarbon feedstock may include, in whole or in part, a gas oil (e.g., light, medium, or heavy gas oil) having an initial boiling point above 200° C., a 50% point of at least 260° C. and an end point of at least 350° C. The feedstock may also include vacuum gas oils, thermal oils, residual oils, cycle stocks, whole top crudes, tar sand oils, shale oils, synthetic fuels, heavy hydrocarbon fractions derived from the destructive hydrogenation of coal, tar, pitches, asphalts, hydrotreated feedstocks derived from any of the foregoing. The hydrocarbon feed can be, isoparaffins, normal-paraffins, neoparaffins, cyclic paraffins, or mixtures thereof, such as a naphtha feed comprising one or more C3-C50 cyclic alkanes (e.g., cyclopropane, cyclobutane, cyclopentane, cyclohexane, cycloheptane, cyclooctane, or mixtures thereof), one or more C2-C50 acyclic alkanes (e.g, n-propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof), or a mixture thereof (e.g., n-pentane, iso-pentane, cyclo-pentane, and or neo-pentane).

Heavy naphtha may include both paraffins and naphthenes (e.g., coal, shale, or petroleum). For example, a naphtha may include from about 15 wt % to about 30 wt % paraffins, from about 5 wt % to about 20 wt % cyclo-paraffins, from about 10 wt % to about 30 wt % olefins, from about 1 wt % to about 10 wt % cycloolefins, and from about 10 wt % to about 40 wt % aromatics. Heavy naphtha can be converted to olefins, such as mono-olefins, using dehydrogenation. The heavy naphtha feed can be processed "as-is", or optionally separated into paraffin and naphthene fractions, or further fractionated to individual carbon number. Dehydrogenation processes of the present disclosure include the dehydrogenation of C2-C50 acyclic alkanes and C3-C50 cyclic alkanes in a heavy naphtha range (e.g., coker naphtha; catalytic naphtha), including paraffins and or naphthenes, to form C2-C50 acyclic olefins and C3-C50 cyclic olefins. The paraffins can be in a gaseous and or a liquid state. In at least one embodiment, the hydrocarbon feed comprises one or more C3-C50 cyclic alkane and one or more C2-C50 acyclic alkane, and a molar ratio of cyclic alkane to acyclic alkane is from about 1:250 to about 250:1, such as from 1:10 to 10:1.

FIG. 1 illustrates a chemical looping process for dehydrogenation and or dehydrogenative coupling, and regeneration of the metal oxide(s) using air. The chemical looping process in which a metal oxide (M1)a(M2)b(M3)c(M4)dOz (I) and or (M1)aOz (II) can be cyclically reduced to form a second metal oxide that is then oxidized while a paraffin feed can be converted via dehydrogenation to a corresponding olefin and or converted via dehydrogenative coupling to heavier hydrocarbon products. In the cyclic (chemical looping or pulsed feed) mode, fine droplets or vapor of the fuel and air can be introduced over the metal oxide bed along with a carrier gas. The feed to the bed can be switched between the resulting mixture and any suitable oxidizing agent (e.g., air). Alternatively, air can be fed continuously to the bed and the liquid feed can be delivered to the reactor (as droplets or vapor) intermittently (as pulsed feed), for example. Finally, the liquid feed may be continuously or semi-continuously fed into a reactor containing the metal oxide(s) (e.g., (M1)a(M2)b(M3)c(M4)dOz (I) and or (M1)aOz (II)), such as a catalytic reduction unit, which continuously circulates between the reactor (e.g., catalytic reduction unit) and a regenerator in which the second metal oxide(s) (M1)a(M2)b(M3)c(M4)dOz-1 and or (M1)aOz-1 can be oxidized (e.g., catalytic oxidation unit). Furthermore, the feed to the reactor can be switched between air and a gaseous fuel (natural gas, or other hydrocarbons). Alternatively, the fuel may be fed to a reactor (e.g., catalytic reduction unit) in which one or more metal oxide(s) (e.g., (M1)a(M2)b(M3)c(M4)dOz (I) and or (M1)aOz (II)) can be continuously circulated between a fuel partial oxidation reactor and a regenerator (e.g., catalytic oxidation unit).

In at least one embodiment, the hydrocarbon feedstock conversion, such as the paraffin conversion, to C3-C50 cyclic olefins, C2-C50 acyclic olefins, and or C5-C200 hydrocarbon products, such as C5-C100 heavier hydrocarbon products, is performed at an metal oxide (e.g., (M1)a(M2)b(M3)c(M4)dOz (I) and or (M1)aOz (II))/paraffin molar ratio of from 1,000:1 to 1:1,000, such as from 100:1 to 1:100, such as from 50:1 to 1:50, such as from 10:1 to 1:10.

The hydrocarbon feedstock conversion, such as the paraffin conversion, to C3-C50 cyclic olefins, C2-C50 acyclic olefins, and or C5-C200 hydrocarbon products, such as C5-C100 hydrocarbon products, can be performed at a temperature of from about 50° C. to about 500° C., such as from about 75° C. to about 450° C., such as from about 100° C. to about 400° C., such as from about 150° C. to about 300° C. (e.g., 250° C.).

In at least one embodiment, the hydrocarbon feedstock conversion, such as the paraffin conversion, to C3-C50 cyclic olefins, C2-C50 acyclic olefins, and or C5-C200 hydrocarbon products, such as C5-C100 hydrocarbon products, is performed at a pressure of from about 15 psig to about 2,000 psig, such as from about 15 psig to about 1,000 psig, such as from about 15 psig to about 500 psig.

The hydrocarbon feedstock conversion, such as the paraffin conversion, to C3-C50 cyclic olefins, C2-C50 acyclic olefins, and or C5-C200 hydrocarbon products, such as C5-C100 hydrocarbon products, can be performed at a residence time of about 1 milli-second to about 48 hours, such as about 10 milli-seconds to about 24 hours, such as about 5 minutes to about 20 hours.

In at least one embodiment, the metal oxide(s) (e.g., (M1)a(M2)b(M3)c(M4)dOz-1 and or (M1)aOz-1 regeneration process is performed at a temperature of from about 50° C. to about 1,000° C., such as from about 75° C. to about 750° C., such as from about 100° C. to about 500° C., such as from about 150° C. to about 300° C. (e.g., 250° C.); at a pressure of from about 15 psig to about 2,000 psig, such as from about 50 psig to about 1,500 psig, such as from about 100 psig to about 1,000 psig; at a residence time of about 1 milli-second to about 48 hours, such as about 10 milli-seconds to about 24 hours, such as about 5 minutes to about 20 hours.

The hydrocarbon feed may contain one or more hydrocarbon feeds described above. A dehydrogenation process, and or a dehydrogenative coupling process, can involve contacting a C3-C50 cyclic alkane and or a C2-C50 acyclic alkane feed with one or more metal oxide(s) (e.g., (M1)a(M2)b(M3)c(M4)dOz (I) and or (M1)aOz (II)) including platinum group metals, alloys, oxides, carbides, nitrides, and or sulfides of individual transition metal and or a mixed metal compound. The metal oxide(s) (e.g., (M1)a(M2)b(M3)c(M4)dOz (I) and or (M1)aOz (II)) can be bulk and or supported. Suitable supports include non-acidic oxides including silica, theta-alumina, zirconia, titania, ceria, non-acidic clays, or basic oxides (such as magnesia, hydrotalcites, or lanthanum oxide). The metal oxide may include a transition metal oxide, such as CuO, Ag2O, ZnO, NiO, CoOz, FeOz, MnOz, CrOz, or VOz, for example, or mixtures thereof, where z is in the range of 1 to 3.5. In at least one embodiment, the dehydrogenation process, and or a dehydrogenative coupling process, of C3-C50 cyclic alkane and or a C2-C50 acyclic alkane, is mediated using one or more metal oxide(s) selected from CuO, CuO2, Ag2O, Na2O2, ZnO, ZnO2, NiO, Ni2O3, CrOz, VOz, FeOz, Fe2O3, CoOz, Co2O3, Co3O4, MnOz, BaO2, CuO/SiO2 CuO/Al2O3 VOz/Al2O3, YMnO4, YMnO3.5, and or MgO2. The C2-C50 acyclic olefins products, C3-C50 cyclic olefins products, and or C5-C200 hydrocarbon products, such as C5-C100 hydrocarbon products, can be substituted and or non-substituted olefins products. In at least one embodiment, the product mixture is substantially free of H2 (e.g., <500 ppm, such as <100 ppm, such as <10 ppm, such as <5 ppm, such as <1 ppm)).

In a dehydrogenation process, and or a dehydrogenative coupling process, a feed stream including at least 2 wt % of C2 to C50 cyclic alkanes and or C2 to C50 acyclic alkanes can be contacted with a metal oxide suitable for a dehydrogenation process and or a dehydrogenative coupling process, with or without the presence of a solvent, such as the hydrocarbons including C2 to C50 cyclic alkanes and or C2 to C50 acyclic alkanes of the feed stream can be used directly as solvent.

Optionally one or more solvent(s) can be used for a process of the present disclosure. The solvent may be a saturated hydrocarbon or an aromatic solvent such as n-hexane, n-heptane, cyclohexane, benzene, toluene, xylenes, or a mixture thereof. Contacting the metal oxide with a feedstream comprising the C2 to C50 alkanes may be carried out in an atmosphere inert under the process conditions, such as in nitrogen, argon, or a mixture thereof. Naphtha, including both paraffins and naphthenes, may include various ranges of cyclic and acyclic alkanes. For example, C3-C50 cyclic alkanes can be cyclopentane, cyclobutane, cyclopentane, cyclohexane, cycloheptane, cyclooctane. Examples of C2-C50 acyclic alkanes can be n-propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof.

A molar ratio of one or more cyclic alkanes to acyclic alkanes can be from about 1:1,000 to about 1,000:1, such as from about 1:700 to about 700:1, such as from about 1:500 to about 500:1, such as from about 1:250 to about 250:1, such as from about 1:100 to about 100:1, such as from about 1:50 to about 50:1, such as from about 1:10 to about 10:1.

In at least one embodiment, a dehydrogenation process, and or a dehydrogenative coupling process, is performed at a temperature of 500° C. or less, such as from about 100° C. to about 450° C., such as from about 150° C. to about 350° C. (e.g., 275° C.). A dehydrogenation process, and or a dehydrogenative coupling process, of the present disclosure may be carried out by mixing a solution of C3-C50 cyclic alkanes and C2-C50 acyclic alkanes and one or more metal oxide(s), cooling the solution, and optionally allowing the mixture to increase in temperature.

In at least one embodiment, the process for the production of one or more C3-C50 cyclic olefins, one or more C2-C50 acyclic olefins, one or more C5-C200 hydrocarbons (such as C5-C100 heavier hydrocarbons), or a mixture thereof, includes: dehydrogenating, and or dehydrogenating coupling process, at least one C2-C50 acyclic alkane and at least one C3-C50 cyclic alkane by contacting the at least one C2-C50 acyclic alkane and the at least one C3-C50 cyclic alkane with one or more metal oxide(s) (e.g., (M1)a(M2)b(M3)c(M4)dOz (I) and or (M1)aOz (II)) in at least one solution dehydrogenation/dehydrogenative coupling reactor at a reactor pressure of from about 15 psig to about 2,000 psig, and or a reactor temperature of from about 100° C. to about 450° C. The C2-C50 acyclic olefins, C3-C50 cyclic olefins products, and or C5-C200 hydrocarbons (such as C5-C100 heavier hydrocarbons) can be recovered and analyzed by GC.

Metal Oxides for Dehydrogenation and Dehydrogenative Coupling Processes

In at least one embodiment, the conversion of paraffins (e.g., isoparaffins, normal-paraffins, neoparaffins, cyclic paraffins, or mixtures thereof) to one or more C3-C50 cyclic olefins, one or more C2-C50 acyclic olefins, one or more C5-C200 hydrocarbons (such as C5-C100 heavier hydrocarbons), or a mixture thereof, is performed using a metal oxide, also referred to as metal oxide, that is represented by Formula (I):

$$(M1)a(M2)b(M3)c(M4)dOz \quad (I)$$

wherein:
M1 is a group 1, 2, 3, 4, 5, 6, 7, 8, 9, 10, 11, 12, 13, 14, 15, 16, or 17 metal;
M2 is a group 1, 2, 3, 4, 5, 6, 7, 8, 9, 10, 11, 12, 13, 14, 15, 16, or 17 metal;
M3 is a group 1, 2, 3, 4, 5, 6, 7, 8, 9, 10, 11, 12, 13, 14, 15, 16, or 17 metal;
M4 is a group 1, 2, 3, 4, 5, 6, 7, 8, 9, 10, 11, 12, 13, 14, 15, 16, or 17 metal;
a is $0.01 \leq a \leq 4$;
b is $0 \leq b \leq 4$;
c is $0 \leq c \leq 4$;
d is $0 \leq d \leq 4$; and
z is $1 \leq z \leq 12$.

In an alternate embodiment, b, c, d of Formula (I) is 0 and the metal oxide is represented by Formula (II):

$$(M1)aOz \quad (II)$$

wherein:
M1 is a group 1, 2, 3, 4, 5, 6, 7, 8, 9, 10, 11, 12, 13, 14, 15, 16, or 17 metal;
a is $0.01 \leq x \leq 4$; and
z is $1 \leq z \leq 12$.

Suitable examples of metal oxide (M1)a(M2)b(M3)c(M4)dOz (I) can be, but are not limited to, CuO/SiO2 CuO/Al2O3 VOz/Al2O3, YMnO4, YMnO3.5, where z is in the range of 1 to 3.5 Suitable examples of metal oxide (M1)aOz (II) can be, but are not limited to, CuO, CuO2, Ag2O, Na2O2, ZnO, ZnO2, NiO, Ni2O3, CrOz, VOz, FeOz, Fe2O3, CoOz, Co2O3, Co3O4, MnOz, BaO2, MgO2, where z is in the range of 1 to 3.5

Metal oxide(s) (M1)a(M2)b(M3)c(M4)dOz (I) and or (M1)aOz (II) of the present disclosure may include platinum group metals (e.g., Pd, Rh, Pt), alloys (e.g., bimetallic Pt—Fe catalysts, Cu—Al alloy catalyst, Pt—Zn alloy nanocluster catalyst), oxides, carbides (e.g., bulk W—Mo mixed carbides, Mo carbide modified nanocarbon catalysts), nitrides (e.g., B—N catalyst), and or sulfides (e.g., Mo-sulfide-alumina catalyst) of individual transition metal and or mixed metal catalyst. The metal oxide(s) (e.g., (M1)a(M2)b(M3)c(M4)dOz (I) and or (M1)aOz (II)) can be bulk and or supported. The metal oxide(s) (e.g., (M1)a(M2)b(M3)c(M4)dOz (I) and or (M1)aOz (II)) may include a transition metal oxide, such as copper oxide (CuO), silver oxide (Ag2O), zinc oxide (ZnO), nickel oxide (NiO), chromium oxide (CrOz), or vanadium oxide (VOz), CoOz, FeOz, MnOz, for example, or mixtures thereof, where z is in the range of 1 to 3.5.

For purposes of the present disclosure, a metal oxide loading % (based on the concentration of the alkanes) can be from about 0.01 mol % to about 50 mol %, such as from about 0.1 mol % to about 25 mol %, such as from about 0.2 mol % to about 10 mol %, such as from about 0.5 mol % to about 5 mol %, such as about 0.2 mol %, for example.

The paraffin dehydrogenation to olefins, as well as the dehydrogenative coupling to heavier paraffins, are thermodynamically unfavored, and conversions are equilibrium limited, i.e. no matter how effective a catalyst is, the best conversion the catalyst can achieve is what the reaction equilibrium will allow. The free energy ΔG (kcal/mol) for the dehydrogenation reaction can only become favorable when the temperature is at least about 600° C. Consequently, a large amount of energy is needed in order to enable the dehydrogenation reaction and the dehydrogenative coupling. In addition, the catalysts tend to deactivate quickly due to coking, and frequent regeneration can be necessary. In the case of dehydrogenative coupling, the free energy ΔG (kcal/mol) becomes favorable at very low temperatures (e.g., <0° C.). In contrast, when using a metal oxide (e.g., CuO) for the paraffin dehydrogenation to olefins, as well as the dehydrogenative coupling to heavier paraffins, the free energy becomes much more favorable for dehydrogenation, for example, with a free energy becoming negative (e.g., ΔG of from about 0 kcal/mol to about −100 kcal/mol, such as from about −5 kcal/mol to about −75 kcal/mol), and or at a temperature range of from 0° C. to 1,000° C., thus eliminating the equilibrium limitation.

Hence, the redox metal oxides can enable the conversion processes of the hydrocarbon feedstocks to be thermodynamically favorable, thus allowing the dehydrogenation reaction, as well as the dehydrogenative coupling, to occur at much lower temperatures than that of conventional processes (e.g., ≤500° C.). Processes of the present disclosure can enable reducing the energy intensity and the greenhouse gas emissions. While similar effects can be achieved using alternative strategies such as oxidative dehydrogenation or selective hydrogen combustion, both of these processes need a co-feed of O2 with hydrocarbons, which can create a combustible air/fuel mix. Additionally, a direct contact of O2 with hydrocarbons can result in undesired radicals and gas phase reactions, leading to over-oxidation and low selectivity of the conventional catalysts to the hydrocarbon feedstock (e.g., selectivity of about 45% or lower).

Metal oxides (e.g., $(M1)_a(M2)_b(M3)_c(M4)_dO_z$ (I) and or $(M1)_aO_z$ (II)) utilized in the processes described herein can be prepared by any suitable technique such as co-precipitation, urea precipitation, or sol-gel synthesis. The metal oxide oxygen carryings (e.g., $(M1)_a(M2)_b(M3)_c(M4)_dO_z$ (I) and or $(M1)_aO_z$ (II)) may take the form of granules, pellets, or monolithic structures. Coal ash may also be used as a support for selected unary (e.g., $Fe_2O_3$, $Fe_3O_4$, $MnO_z$, $CoO_z$, and $NiO_z$) and binary (e.g., $FeTiO_3$, $Mn_{1-x}Cu_yO_z$, and $Mn_{1-x}Fe_yO_z$) metal oxides. The metal oxide materials (e.g., $(M1)_a(M2)_b(M3)_c(M4)_dO_z$ (I) and or $(M1)_aO_z$ (II)) and coal ash may be bound with an inorganic binder such as silica, titania, magnesia, boehmite, or zirconia. As indicated above, fixed beds of the metal oxides (e.g., $(M1)_a(M2)_b(M3)_c(M4)_dO_z$ (I) and or $(M1)_aO_z$ (II)) may be either exposed to alternating air and feed, or to a continuous feed of air and intermittent (pulsed) feed of feedstock. In at least one embodiment, fluidized bed systems comprise one, two, or more fluidized beds. Alternating exposure to air and hydrocarbons feed can be achieved either by means of a set of valves (for a single bed) or in the case of two or more beds by circulation of the oxygen carrier between the reactor and regenerator beds.

The first metal oxides (e.g., $(M1)_a(M2)_b(M3)_c(M4)_dO_z$ (I) and or $(M1)_aO_z$ (II)) can be regenerated by oxidizing the second metal oxides (e.g., $(M1)_a(M2)_b(M3)_c(M4)_dO_{z-1}$ and or $(M1)_aO_{z-1}$), since the metal oxides are oxygen carriers, thus enabling oxidative conversions without directly contacting O2 with the feed. Air can be used for purposes of the present disclosure (instead of pure O2 in the cases of oxidative dehydrogenation and selective hydrogen combustion), which also reduces the cost and energy intensity of the process.

In addition to the reactivity toward paraffins, and the capability of regeneration via air, the active oxygen content, or oxygen capacity, is another important parameter in selecting the metal oxides (e.g., $(M1)_a(M2)_b(M3)_c(M4)_dO_z$ (I) and or $(M1)_aO_z$ (II)). The oxygen capacity is calculated using the following (using $MO_z$ and $MO_{(z-1)}$ to represent the first metal oxide and the second metal oxide, respectively):

$$\text{Oxygen Capacity} = \frac{\text{Oxygen wt \% in } MO_z \text{ per mole of metal} - \text{Oxygen wt \% in } MO(z-1) \text{ per mole of metal}}{O \text{ wt \% in } MO_z \text{ per mole of metal}}$$

In at least one embodiment, the oxygen capacity of metal oxide(s) (e.g., $(M1)_a(M2)_b(M3)_c(M4)_dO_z$ (I) and or $(M1)_aO_z$ (II)) is from about 1 wt % to about 50 wt %, based on the weight of the metal oxide, such as from about 2 wt % to about 45 wt %, such as from about 3 wt % to about 35 wt %, such as from about 10 wt % to about 35 wt %, such as from about 15 wt % to about 35 wt %, such as from about 20 wt % to about 30 wt %, such as from about 20 wt % to about 28 wt %, alternatively from about 8 wt % to about 18 wt %, such as from about 10 wt % to about 16 wt %.

Optional Support Materials for Dehydrogenation Metal Oxides

In embodiments herein, the oxygen carrying system may include an inert support material. The supported material can be a porous support material, for example, talc, and inorganic oxides. Suitable supports are non-acidic oxides including silica, theta-alumina, zirconia, titania, ceria, non-acidic clays, or basic oxides (such as magnesia, hydrotalcites, or lanthanum oxide). Other support materials may include zeolites, organoclays, or another organic or inorganic support material, or mixtures thereof.

The support material can be an inorganic oxide in a finely divided form. Suitable inorganic oxide materials for use in oxygen carrying systems herein include groups 2, 4, 10, 11, 12, 13, and 14 metal oxides, such as silica, alumina, MgO, $TiO_2$, $ZrO_2$, rare-earth oxides (e.g., $La_2O_3$, $CeO_2$), and mixtures thereof. Other inorganic oxides that may be employed either alone or in combination with the silica, or alumina, are magnesia, titania, zirconia. Suitable supports may include magnesia, titania, zirconia, montmorillonite, phyllosilicate, zeolites, talc, clays. Also, combinations of these support materials may be used, for example, silica-chromium, silica-alumina, silica-titania. Support materials include $Al_2O_3$, $ZrO_2$, $SiO_2$, and combinations thereof, such as $SiO_2$, $Al_2O_3$, or $SiO_2/Al_2O_3$.

The support material should be dry, that is, free of absorbed water. Drying of the support material can be effected by heating or calcining at about 100° C. to about 1,000° C., such as at least about 600° C. When the support material is silica, it is heated to at least 200° C., such as about 200° C. to about 850° C., such as at about 600° C.; and or for a time of about 1 minute to about 100 hours, from about 12 hours to about 72 hours, or from about 24 hours to about 60 hours. The calcined support material must have at least some reactive hydroxyl (OH) groups to produce supported metal oxide systems of the present disclosure. The calcined support material is then contacted with at least one metal oxide (e.g., $(M1)_a(M2)_b(M3)_c(M4)_dO_z$ (I) and or $(M1)_aO_z$ (II)).

The support material, having reactive surface groups, such as hydroxyl groups, can be slurried in a non-polar solvent and the resulting slurry can be contacted with a solution of a metal oxide(s). In at least one embodiment, the slurry of the support material is first contacted with a metal oxide, such as $(M1)_a(M2)_b(M3)_c(M4)_dO_z$ (I) and or $(M1)_aO_z$ (II)) metal oxides, for a period of time in the range of from about 0.5 hours to about 24 hours, from about 2 hours to about 16 hours, or from about 4 hours to about 8 hours.

One or more metal oxide(s) (e.g., $(M1)_a(M2)_b(M3)_c(M4)_dO_z$ (I) and or $(M1)_aO_z$ (II)) and support can be heated to about 0° C. to about 70° C., such as about 23° C. to about 60° C., such as at room temperature. Contact times may range from about 0.5 hours to about 24 hours, from about 2 hours to about 16 hours, or from about 4 hours to about 8 hours.

Suitable non-polar solvents can be materials in which all of the reactants used herein, e.g., the first metal oxide and the second metal oxide are at least partially soluble and which are liquid at reaction temperatures. Non-polar solvents can be alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Dehydrogenation Products

The present disclosure relates to compositions of matter produced by the methods described herein. Furthermore, commercially valuable products such as ethylene and propylene can be formed using processes of the present disclosure.

In at least one embodiment, a process described herein produces C2-C50 acyclic olefins of Formula (III) (such as propene, butene, pentene, hexene, heptene, octene, etc., and any isomers thereof), and C3-C50 cyclic olefins of Formula (IV) (such as cyclopentene, methyl-cyclopentene, cyclohexene, cycloheptene, cyclooctene, norbornene, etc., and any isomers thereof).

In at least one embodiment, an acyclic olefin is represented by formula (III):

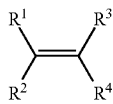

(III)

wherein:
R1, R2, R3, and R4 are independently hydrogen, C1-C40 hydrocarbyl (e.g., C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), C1-C40 substituted hydrocarbyl (e.g., substituted C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), a heteroatom or a heteroatom-containing group, such as each of R1, R2, R3, and R4 is independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may be halogenated (such as bromopropyl, bromopropyl, bromobutyl, (bromomethyl)cyclopropyl, chloroethyl, 2,3,5,6-tetrafluorobenzyl, perfluoropropyl, perfluorobutyl, perfluoroethyl, perfluoromethyl), substituted hydrocarbyl radicals and isomers of substituted hydrocarbyl radicals such as trimethylsilylpropyl, trimethylsilylmethyl, trimethylsilylethyl, phenyl, or isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyle. In at least one embodiment, R2 and R3 are independently hydrogen or C1-C40 hydrocarbyl (e.g., C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), substituted hydrocarbyl (e.g., substituted C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), such as methyl, ethyl, propyl, butyl, pentyl, hexyl, heptyl, octyl, nonyl, decyl, undecyl, dodecyl, phenyl, substituted phenyl, biphenyl or an isomer thereof, such as perfluoropropyl-, perfluorobutyl-, perfluoroethyl-, or perfluoromethyl-substituted hydrocarbyl radicals and isomers of substituted hydrocarbyl radicals such as trimethylsilylpropyl, trimethylsilylmethyl, trimethylsilylethyl, or phenyl, and isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl; and R1 and R4 are independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may be halogenated (such as bromopropyl, bromopropyl, bromobutyl, (bromomethyl)cyclopropyl, chloroethyl, 2,3,5,6-tetrafluorobenzyl, perfluoropropyl, perfluorobutyl, perfluoroethyl, perfluoromethyl), substituted hydrocarbyl radicals and isomers of substituted hydrocarbyl radicals such as trimethylsilylpropyl, trimethylsilylmethyl, trimethylsilylethyl, phenyl, or isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl.

In at least one embodiment, R2 and R3 are hydrogen and R1 and R4 are independently selected from hydrogen, methyl, ethyl, propyl, butyl, pentyl, hexyl, heptyl, octyl, nonyl, decyl, undecyl, dodecyl, phenyl, substituted phenyl, biphenyl or an isomer thereof, which may include oxygen, nitrogen, and or sulfur (such as methoxypropyl, methoxybutyl, methoxypentyl methoxyhexyl, methoxyheptyl, methoxyoctyl, methoxydodecyl, ethoxyethyl, ethoxypropyl, ethoxybutyl, ethoxypentyl ethoxyhexyl, ethoxyheptyl, ethoxyoctyl, ethoxyldecyl, ethoxydodecyl, ethoxyphenyl, 1-aminoalkyl (e.g., 1-aminobutyl), 2-aminoalkyl (e.g., 2-aminopentyl), 1-alkylaminoalkyl (e.g., 1-methylaminopropyl), dialkylaminoalkyl (e.g., dimethylaminoethyl) or isomers of hydrocarbyl substituted phenyl such as methylphenyl, dimethylphenyl, trimethylphenyl, tetramethylphenyl, pentamethylphenyl, diethylphenyl, triethylphenyl, propylphenyl, dipropylphenyl, tripropylphenyl, dimethylethylphenyl, dimethylpropylphenyl, dimethylbutylphenyl, and dipropylmethylphenyl.

For example, the acyclic olefin represented by formula (III) can be a vinylenes, such as an olefin with a "cis-" conformation, such as an olefin with "trans-" conformation, or a mixture thereof, thus at any proportion thereof. Furthermore, the acyclic olefin can be a tri-substituted vinylene. Traces of tetra-substituted vinylene may be present in the reaction mixture.

In at least one embodiment, a cyclic olefin compound is represented by formula (II):

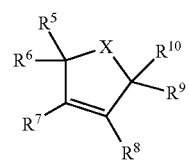

(IV)

wherein:
X is a one-atom to five-atom linkage (with a "one-atom" linkage referring to a linkage that provides a single, optionally substituted atom between the two adjacent carbon atoms, and a "five-atom" linkage, similarly, referring to a linkage that provides five optionally substituted atoms between the two adjacent carbon atoms); In at least one embodiment, and when the cyclic olefin is bicyclic (e.g., when R5 and R10 are linked), then X is a one-atom or two-atom linkage, such as a linkage that has one or two optionally substituted atoms between the two carbon atoms to which X is bound. For example, X can be of the formula —CR11R12-(X1)q- wherein q is zero or 1, X1 is CR13R14, O, S, or NR15, and R11, R12, R13, R14, and R15 are independently selected from hydrogen, hydrocarbyl (e.g., C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), substituted hydrocarbyl (e.g., substituted C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), heteroatom-containing hydrocarbyl (e.g., C1-C20 heteroalkyl, C5-C20 heteroaryl, heteroatom-containing C5-C30 aralkyl, or heteroatom-containing C5-C30 alkaryl), substituted heteroatom-containing hydrocarbyl (e.g., substituted C1-C20 heteroalkyl, C5-C20 heteroaryl, heteroatom-containing C5-C30 aralkyl, or heteroatom-containing C5-C30 alkaryl); When q is 1, suitable examples of linkages can be wherein X1 is CR13R14, thus providing a substituted or unsubstituted ethylene moiety to the cyclic olefin of Formula (IV). Accordingly, when R11, R12, R13, and R14 are hydrogen, then X is ethylene. When q is zero, the linkage can be substituted or unsubstituted methylene, and a suitable linkage within this group can be methylene (e.g., when R11 and R12 are both hydrogen);

At least one of R7 and R8 is hydrogen and the other is selected from hydrogen, hydrocarbyl (e.g., C1-C20 alkyl, C2-C20 alkenyl, C2-C20 alkynyl, C5-C20 aryl, C6-C24 alkaryl, and C6-C24 aralkyl), substituted hydrocarbyl (e.g., substituted C1-C20 alkyl, C2-C20 alkenyl, C2-C20 alkynyl, C5-C20 aryl, C6-C24 alkaryl, and C6-C24 aralkyl), heteroatom-containing hydrocarbyl (e.g., heteroatom-containing C1-C20 alkyl, C2-C20 alkenyl, C2-C20 alkynyl, C5-C20 aryl, C6-C24 alkaryl, and C6-C24 aralkyl), or substituted heteroatom-containing hydrocarbyl (e.g., substituted heteroatom-containing C1-C20 alkyl, C2-C20 alkenyl, C2-C20 alkynyl, C5-C20 aryl, C6-C24 alkaryl, and C6-C24 aralkyl); and R5, R6, R9, and R10 are independently selected from hydrogen, hydrocarbyl (e.g., C1-C20 alkyl, C5-C20 aryl, C5-C30 aralkyl, or C5-C30 alkaryl), substituted hydrocarbyl (e.g., substituted C1-C20 alkyl, C5-C20 aryl, C5-C30 aralkyl, or C5-C30 alkaryl), heteroatom-containing hydrocarbyl (e.g., C1-C20 heteroalkyl, C5-C20 heteroaryl, heteroatom-containing C5-C30 aralkyl, or heteroatom-containing C5-C30 alkaryl), substituted heteroatom-containing hydrocarbyl (e.g., substituted C1-C20 heteroalkyl, C5-C20 heteroaryl, heteroatom-containing C5-C30 aralkyl, or heteroatom-containing C5-C30 alkaryl). Additionally, any two or more of R5, R6, R9, and R10 can be taken together to form a cyclic group, which may be, for example, five- or six-membered rings, or two or three five- or six-membered rings, which may be either fused or linked. The cyclic groups may be aliphatic or aromatic, and may be heteroatom-containing and or substituted.

One group of such cyclic olefins are those of formula (IV) wherein R6 and R10 are hydrogen, R5 is and R9 combine to form a cyclic ring. In such embodiments, the cyclic olefin is represented by Formula (V):

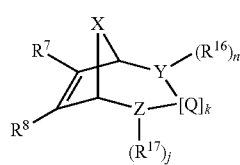

(V)

wherein:
X is a one-atom to five-atom linkage. In at least one embodiment, and when the cyclic olefin is bicyclic (e.g., when R5 and R10 are linked), then X is a one-atom or two-atom linkage, such as a linkage that has one or two optionally substituted atoms between the two carbon atoms to which X is bound. For example, X can be of the formula —CR11R12-(X1)q- wherein q is zero or 1, X1 is CR13R14, O, S, or NR15, and R11, R12, R13, R14, and R15 are independently selected from hydrogen, hydrocarbyl (e.g., C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), substituted hydrocarbyl (e.g., substituted C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), heteroatom-containing hydrocarbyl (e.g., C1-C20 heteroalkyl, C5-C20 heteroaryl, heteroatom-containing C5-C30 aralkyl, or heteroatom-containing C5-C30 alkaryl), substituted heteroatom-containing hydrocarbyl (e.g., substituted C1-C20 heteroalkyl, C5-C20 heteroaryl, heteroatom-containing C5-C30 aralkyl, or heteroatom-containing C5-C30 alkaryl); When q is 1, suitable examples of linkages can be wherein X1 is CR13R14, thus providing a substituted or unsubstituted ethylene moiety to the cyclic olefin of Formula (V). Accordingly, when R11, R12, R13, and R14 are hydrogen, then X is ethylene. When q is zero, the linkage can be substituted or unsubstituted methylene, and a suitable linkage within this group can be methylene (e.g., when R11 and R12 are both hydrogen);

At least one of R7 and R8 is hydrogen and the other is selected from hydrogen, hydrocarbyl (e.g., C1-C20 alkyl, C2-C20 alkenyl, C2-C20 alkynyl, C5-C20 aryl, C6-C24 alkaryl, and C6-C24 aralkyl), substituted hydrocarbyl (e.g., substituted C1-C20 alkyl, C2-C20 alkenyl, C2-C20 alkynyl, C5-C20 aryl, C6-C24 alkaryl, and C6-C24 aralkyl), heteroatom-containing hydrocarbyl (e.g., heteroatom-containing C1-C20 alkyl, C2-C20 alkenyl, C2-C20 alkynyl, C5-C20 aryl, C6-C24 alkaryl, and C6-C24 aralkyl), or substituted heteroatom-containing hydrocarbyl (e.g., substituted heteroatom-containing C1-C20 alkyl, C2-C20 alkenyl, C2-C20 alkynyl, C5-C20 aryl, C6-C24 alkaryl, and C6-C24 aralkyl);
Y and Z are independently N, O, or S;
k is zero or 1;
j and n are independently zero or 1;
Q is a one-atom to five-atom linkage. In at least one embodiment, and when the cyclic olefin is bicyclic (e.g., when R16 and R17 are linked), then Q is a one-atom or two-atom linkage, such as a linkage that has one or two optionally substituted atoms between the two carbon atoms to which Q is bound. For example, Q can be of the formula —CR11'R12'-(Q1)q'- wherein q' is zero or 1, Q1 is CR13'R14', O, S, or NR15', and R11', R12', R13', R14', and R15' are independently selected from hydrogen, hydrocarbyl (e.g., C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), substituted hydrocarbyl (e.g., substituted C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), heteroatom-containing hydrocarbyl (e.g., C1-C20 heteroalkyl, C5-C20 heteroaryl, heteroatom-containing C5-C30 aralkyl, or heteroatom-containing C5-C30 alkaryl), substituted heteroatom-containing hydrocarbyl (e.g., substituted C1-C20 heteroalkyl, C5-C20 heteroaryl, heteroatom-containing C5-C30 aralkyl, or heteroatom-containing C5-C30 alkaryl); When q' is 1, suitable examples of linkages can be wherein Q1 is CR13'R14', thus providing a substituted or unsubstituted ethylene moiety to the cyclic olefin of Formula (V). Accordingly, when R11', R12', R13', and R14' are hydrogen, then Q is ethylene. When q' is zero, the linkage can be substituted or unsubstituted methylene, and a suitable linkage within this group can be methylene (e.g., when R11' and R12' are both hydrogen); R16 and R17 are independently selected from hydrogen, hydrocarbyl, substituted hydrocarbyl, heteroatom-containing hydrocarbyl, substituted heteroatom-containing hydrocarbyl, and amino groups, wherein R16 and R17 may be taken together to form a cyclic group;
when Y is O or S, then n is zero;
when Z is O or S, then j is zero;
when Y is N, then n is 1; and
when Z is N, then j is 1.

In an alternate embodiment, R6 and R9 of formula (V) are hydrogen, in which case the cyclic olefin is represented by formula (VI):

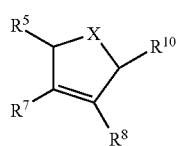

(VI)

wherein:
X is a one-atom to five-atom linkage. In at least one embodiment, and when the cyclic olefin is bicyclic (e.g., when R5 and R10 are linked), then X is a one-atom or two-atom linkage, such as a linkage that has one or two optionally substituted atoms between the two carbon atoms to which X is bound. For example, X can be of the formula —CR11R12-(X1)q- wherein q is zero or 1, X1 is CR13R14, O, S, or NR15, and R11, R12, R13, R14, and R15 are independently selected from hydrogen, hydrocarbyl (e.g., C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), substituted hydrocarbyl (e.g., substituted C1-C20 alkyl, C2-C20 alkenyl, C2-C20 alkynyl, C5-C20 aryl, C6-C24 alkaryl, C6-C24 aralkyl, C1-C20 alkyl, C5-C20 aryl, C5-C30 aralkyl, or C5-C30 alkaryl), heteroatom-containing hydrocarbyl (e.g., C1-C20 heteroalkyl, C5-C20 heteroaryl, heteroatom-containing C5-C30 aralkyl, or heteroatom-containing C5-C30 alkaryl), substituted heteroatom-containing hydrocarbyl (e.g., substituted C1-C20 heteroalkyl, C5-C20 heteroaryl, heteroatom-containing C5-C30 aralkyl, or heteroatom-containing C5-C30 alkaryl). When q is 1, suitable examples of linkages can be wherein X1 is CR13R14, thus providing a substituted or unsubstituted ethylene moiety. Accordingly, when R11, R12, R13, and R14 are hydrogen, then X is ethylene. When q is zero, the linkage can be substituted or unsubstituted methylene, and a suitable linkage within this group can be methylene (e.g., when R11 and R12 are both hydrogen).

In at least one embodiment, one of R7 and R8 is hydrogen and the other is selected from hydrogen, hydrocarbyl (e.g., C1-C20 alkyl, C2-C20 alkenyl, C2-C20 alkynyl, C5-C20 aryl, C6-C24 alkaryl, and C6-C24 aralkyl), substituted hydrocarbyl (e.g., substituted C1-C20 alkyl, C2-C20 alkenyl, C2-C20 alkynyl, C5-C20 aryl, C6-C24 alkaryl, and C6-C24 aralkyl), heteroatom-containing hydrocarbyl (e.g., heteroatom-containing C1-C20 alkyl, C2-C20 alkenyl, C2-C20 alkynyl, C5-C20 aryl, C6-C24 alkaryl, and C6-C24 aralkyl), or substituted heteroatom-containing hydrocarbyl (e.g., substituted heteroatom-containing C1-C20 alkyl, C2-C20 alkenyl, C2-C20 alkynyl, C5-C20 aryl, C6-C24 alkaryl, and C6-C24 aralkyl).

In at least one embodiment, R5, R6, R9, and R10 are independently selected from hydrogen, hydrocarbyl (e.g., C1-C20 alkyl, C5-C20 aryl, C5-C30 aralkyl, or C5-C30 alkaryl), substituted hydrocarbyl (e.g., substituted C1-C20 alkyl, C5-C20 aryl, C5-C30 aralkyl, or C5-C30 alkaryl), heteroatom-containing hydrocarbyl (e.g., C1-C20 heteroalkyl, C5-C20 heteroaryl, heteroatom-containing C5-C30 aralkyl, or heteroatom-containing C5-C30 alkaryl), substituted heteroatom-containing hydrocarbyl (e.g., substituted C1-C20 heteroalkyl, C5-C20 heteroaryl, heteroatom-containing C5-C30 aralkyl, or heteroatom-containing C5-C30 alkaryl). Additionally, two or more of R5, R6, R9, and R10 can be taken together to form a cyclic group, which may be, for example, five- or six-membered rings, or two or three five- or six-membered rings, which may be either fused or linked. The cyclic groups may be aliphatic or aromatic, and may be heteroatom-containing and or substituted.

The C2 to C50 cyclic olefins may be strained or unstrained, monocyclic or polycyclic, and may optionally include heteroatoms and or one or more functional groups. Exemplary monocyclic olefins represented by Formula (IV) (e.g., olefins wherein R5 and R10 are not linked) may include, but are not limited to, cyclopentene, 3-methylcyclopentene, 4-methylcyclopentene, 3-t-butyldimethylsilyloxycyclopentene, 4-t-butyl-dimethylsilyloxycyclopentene, cyclohexene, 3-methylcyclohexene, 4-methyl-cyclohexene, 3-t-butyldimethylsilyloxycyclohexene, 4-t-butyldimethyl silyloxycyclohexene, cycloheptene, 3-methylcycloheptene, 4-methylcycloheptene, 5-methylcycloheptene, 3-t-butyldimethyl silyloxycycloheptene, 4-t-butyldimethyl silyloxycycloheptene, 5-t-butyldimethylsilyloxycycloheptene, cyclooctene, 3-methylcyclooctene, 4-methylcyclooctene, 5-methylcyclooctene, 3-t-butyldimethylsilyloxycyclooctene, 4-t-butyldimethylsilyloxycyclooctene, 5-t-butyldimethylsilyloxycyclooctene, cyclononene, 3-methylcyclononene, 4-methylcyclononene, 5-methylcyclononene, 6-methylcyclo-nonene, 3-t-butyldimethyl silyl oxycyclononene, 4-t-butyldimethyl silyloxycyclononene, 5-t-butyldimethylsilyloxycyclononene, 6-t-butyldimethyl silyloxycyclononene, cyclodecene, 3-methylcyclo-decene, 4-methylcyclodecene, 5-methylcyclodecene, 6-methylcyclodecene, 3-t-butyldimethyl silyloxycyclodecene, 4-t-butyldimethyl silyloxycyclononene, 5-t-butyldimethylsilyloxycyclodecene, 6-t-butyldimethylsilyloxycyclodecene, cycloundecene, 3-methylcycloundecene, 4-methylcycloundecene, 5-methylcycloundecene, 6-methylcycloundecene, 7-methylcycloundecene, 3-t-butyldimethyl silyloxycycloundecene, 4-t-butyldimethylsilyloxycycloundecene, 5-t-butyldimethylsilyloxy-cycloundecene, 6-t-butyldimethylsilyloxycycloundecene, 7-t-butyldimethylsilyloxycycloundecene, cyclododecene, 3-methylcyclododecene, 4-methylcyclododecene, 5-methylcyclododecene, 6-methyl-cyclododecene, 7-methylcyclododecene, 3-t-butyldimethyl silyloxycyclododecene, 4-t-butyldimethyl silyloxycyclododecene, 5-t-butyldimethylsilyloxycyclododecene, 6-t-butyldimethyl silyloxycyclododecene, and 7-t-butyldimethylsilyloxycyclododecene.

Non-limiting examples of cyclic olefins and diolefins may include cyclopropene, cyclobutene, cyclopentene, cyclohexene, cycloheptene, cyclooctene, cyclononene, cyclodecene, norbornene, 4-methylnorbornene, 7-oxanorbornene, 2-methylcyclopentene, 4-methylcyclopentene, vinylcyclohexane, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4- vinylcyclohexane, 1,4-diallylcyclohexane, 1-allyl-5-vinylcyclooctane, and 1,5-diallylcyclooctane.

For example, the cyclic olefin represented by formulae (IV), (V), and (VI) can be a vinylenes, such as an olefin with a "cis-" conformation, such as an olefin with "trans-" conformation, or a mixture thereof, thus at any proportion thereof. Furthermore, the cyclic olefin can be a tri-substituted vinylene. Traces of tetra-substituted vinylene may be present in the reaction mixture.

The C2-C50 acyclic olefins of Formula (III) (such as C2-C20 acyclic olefins, such as C9-C11 acyclic olefins) can be produced with a weight average molecular weight (Mw) of from about 28 g/mol to about 700 g/mol, such as from about 28 g/mol to about 420 g/mol, such as from about 28 g/mol to about 280 g/mol. The C3-C50 cyclic olefins of Formula (III) can be produced with a weight average molecular weight (Mw) of from about 40 g/mol to about 698 g/mol, such as from about 40 g/mol to about 418 g/mol, such as from about 40 g/mol to about 278 g/mol.

Selective conversion of alkanes, such as cyclic alkane (e.g., cycloparaffins) to monoolefins, such as cyclic olefins, is very rare, since the cyclic olefins typically tend to further convert to the most thermodynamically stable products, which are aromatic products (e.g., benzene). Conventionally, catalysts oxidize cyclohexane all the way to benzene, for example, since benzene is the most thermodynamically stable product. Selectivity can be defined as moles of monoolefins divided by moles of the total products formed. In at least one embodiment, metal oxides (I) and or (II) used in processes of the present disclosure have a selectivity for monoolefins (e.g., cyclic olefins such as cyclohexene) of 50% or greater, such as about 50% to about 100%, such as about 55% to about 99.5%, such as from about 70% to about 95%.

Diesel Fuels

In at least one embodiment, a diesel fuel is a C5-C200 hydrocarbon coupling product, such as a C5-C100 hydrocarbon coupling product, such as a C5-C25 hydrocarbon coupling product.

The various types of carbon atoms of a polyolefin product of the present disclosure can be determined using 1H NMR spectroscopy. For example, di-substituted olefin content and tri-substituted olefin content are indicators of linearity of a polyolefin product. A high amount of di-substituted olefin content indicates high linearity, and a low amount of tri-substituted olefin content indicates high linearity. In at least one embodiment, a polyolefin product has a di-substituted olefin content of from about 30% to about 80%, such as from about 50% to about 75%, such as from about 60% to about 70%, based on total unsaturations of the polyolefin product. A polyolefin product of the present disclosure can have a tri-substituted olefin content of less than 50%, based on total unsaturations of the polyolefin product. In at least one embodiment, a polyolefin product has a tri-substituted olefin content of from about 1% to about 50%, such as from about 5% to about 40%, such as from about 20% to about 40%, based on total unsaturations of the polyolefin product. The high linearity of polyolefin products of the present disclosure provides improved cetane number, as compared to highly branched polyolefin products.

Diesel engines may operate well with a cetane number of from 48 to 50. Fuels with a lower cetane number have longer ignition delays, requiring more time for the fuel combustion process to be completed. Hence, higher speed diesel engines operate more effectively with higher cetane number fuels. A hydrocarbon coupling product of the present disclosure can be used as a diesel fuel, as indicated by advantageous cetane numbers. For example, a hydrocarbon coupling product can have a cetane number of about 30 or greater, such as about 40 or greater, such as about 45 or greater, such as about 48 or greater, such as about 50 or greater, such as about 60 or greater, such as about 70 or greater, such as about 80 or greater, such as about 90 or greater.

EXAMPLES

General considerations: All reagents and anhydrous solvents were purchased from Sigma-Aldrich and used as-received.

Figure 2:
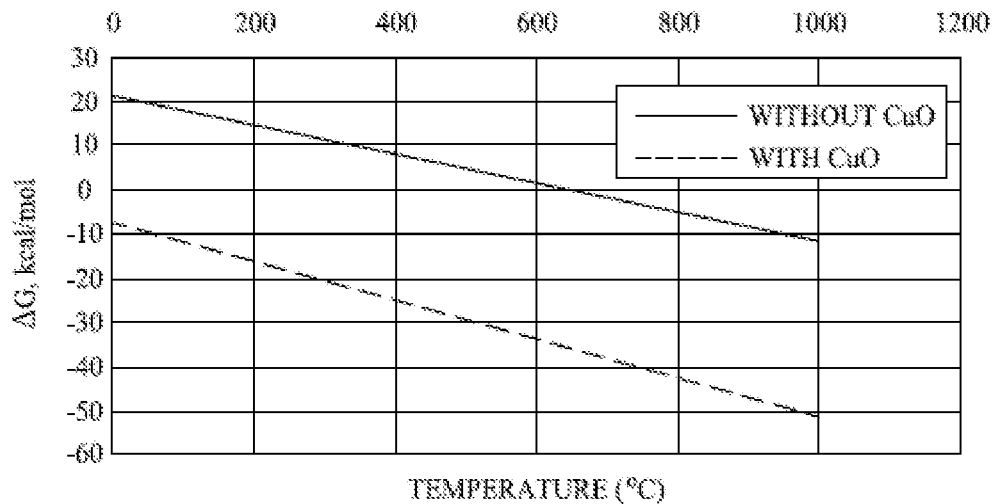
FIG. 2 is a graph illustrating the free energy ΔG (kcal/mol) for propane dehydrogenation as a function of the temperature (° C.), with and without the presence of CuO, according to one embodiment.

The paraffin dehydrogenation to olefins, as well as the dehydrogenative coupling to heavier hydrocarbon products, are both thermodynamically unfavored, and conversions are equilibrium limited. FIG. 2 illustrates the calculated free energy of propane dehydrogenation to propylene in the temperature range of 0° C. to 1,000° C., and under 1 bar of pressure for the following reactions (Eq. 1 and Eq. 2):

$$C3H8\ (g) \rightarrow C3H6\ (g) + H2\ (g) \qquad \text{Eq. 1}$$

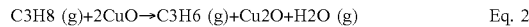
$$C3H8\ (g) + 2CuO \rightarrow C3H6\ (g) + Cu2O + H2O\ (g) \qquad \text{Eq. 2}$$

Typically, the free energy for the dehydrogenation reaction (Eq. 1) only becomes favorable when the temperature is at least about 600° C. Consequently, a large amount of energy is needed in order to enable the dehydrogenation reaction. In addition, the catalysts tend to deactivate quickly due to coking, and frequent catalyst regeneration can be necessary. In contrast, when the dehydrogenation reaction was performed in the presence of a redox active metal oxide, such as CuO, the free energy became much more favorable. For example, when CuO was used, for example, to mediate propane dehydrogenation (Eq. 2), the resulting free energy was negative in the entire temperature range tested, thus eliminating the equilibrium limitations such as performing a dehydrogenation at very high temperature (e.g., 600° C. or greater).

Figure 3:
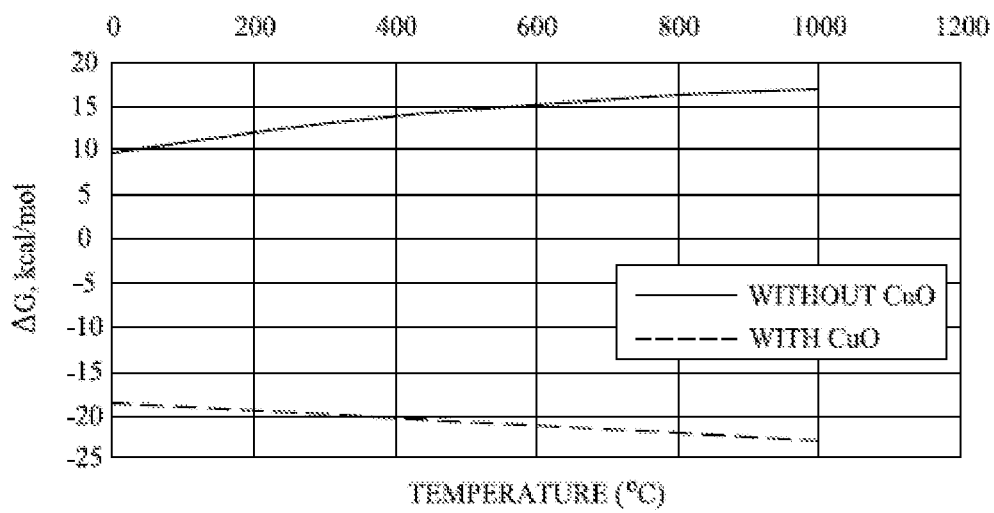
FIG. 3 is a graph illustrating the free energy ΔG (kcal/mol) for propane dehydrogenative coupling as a function of the temperature (° C.), with and without the presence of CuO, according to one embodiment.

Regarding the dehydrogenative coupling of propane to 2,3-dimethylbutane (FIG. 3), the following reactions were used for the free energy calculations:

$$2C3H8(g) C6H14(g) + H2(g) \qquad \text{Eq. 3}$$

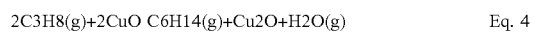
$$2C3H8(g) + 2CuO\ C6H14(g) + Cu2O + H2O(g) \qquad \text{Eq. 4}$$

As shown in FIG. 4, the free energy for the dehydrogenative coupling (Eq. 3) was unfavored in the whole temperature range of 0° C. to 1,000° C., suggesting that the reaction, if possible, can be quite equilibrium limited. However, when the reaction was mediated by a redox active metal oxide, such as CuO (Eq. 4), the free energy was favored in the temperature range of 0° C. to 1,000° C.

Hence, the redox metal oxides enabled the desired conversions to be thermodynamically favorable. Furthermore, the equilibrium limitations were eliminated, thus allowing the dehydrogenation reaction, as well as the dehydrogenative coupling, to occur at much lower temperatures. Processes of the present disclosure can enable reducing the energy intensity and the greenhouse emissions. While similar effects can be achieved using alternative strategies such as oxidative dehydrogenation or selective hydrogen combustion, both processes need a co-feed of O2 with hydrocarbons, which can form a combustible air/fuel mix. Additionally, direct contact of O2 with hydrocarbons can result in undesired radical formation and gas phase reactions, leading to over-oxidation and low selectivity of the conventional catalysts to the hydrocarbon feedstock.

When the first metal oxides were regenerated via oxidation, the net effect was the metal oxides acting as an oxygen carrier, thus enabling oxidative conversions without flowing pure O2 to the reactor. Air was used (instead of pure O2 in the cases of oxidative dehydrogenation and selective hydrogen combustion), which also reduced the cost and energy intensity of the process.

In addition to the reactivity toward paraffins, and the capability of regeneration via air, the active oxygen content, or oxygen capacity, can be another important parameter in selecting the metal oxides. The oxygen capacity of a metal oxide (M1)a(M2)b(M3)c(M4)dOz was calculated using the following (using MOz and MO(z-1) to represent the first metal oxide and the second metal oxide, respectively):

$$\text{Oxygen Capacity} = \frac{\text{Oxygen wt \% in } MOz \text{ per mole of metal} - \text{Oxygen wt \% in } MO(z-1) \text{ per mole of metal}}{O \text{ wt \% in } MOz \text{ per mole of metal}}$$

Table 1 illustrates the oxygen capacity for representative metal oxides, with MgO2 exhibiting the highest oxygen capacity (28.4 wt %).

TABLE 1

| Oxide | From Formula (g/mol) | Reduced oxide | To Formula (g/mol) | Oxygen Capacity (wt %) |
|---|---|---|---|---|
| MgO2 | 56.312 | MgO | 40.312 | 28.4 |
| CaO2 | 72.08 | CaO | 56.08 | 22.2 |
| Na2O2 | 77.982 | Na2O | 61.982 | 20.5 |
| ZnO2 | 97.37 | ZnO | 81.37 | 16.4 |
| Cu2O | 143.08 | Cu | 63.54 | 11.2 |
| CuO | 79.54 | Cu2O | 143.08 | 10.1 |
| Fe2O3 | 159.694 | FeO | 71.84 | 10.0 |
| Ni2O3 | 165.42 | NiO | 74.71 | 9.7 |
| Co2O3 | 165.866 | CoO | 74.933 | 9.6 |
| BaO2 | 169.34 | BaO | 153.34 | 9.4 |
| MnO2 | 86.938 | Mn2O3 | 157.876 | 9.2 |
| YMnO4 | 207.843 | YMnO3 | 191.843 | 7.7 |
| Ag2O | 231.74 | Ag | 107.87 | 6.9 |
| YMnO3.5 | 199.843 | YMnO3 | 191.843 | 4.0 |
| Fe2O3 | 159.694 | Fe3O4 | 231.541 | 3.3 |
| Co2O3 | 165.866 | Co3O4 | 240.799 | 3.2 |

Figure 4A:
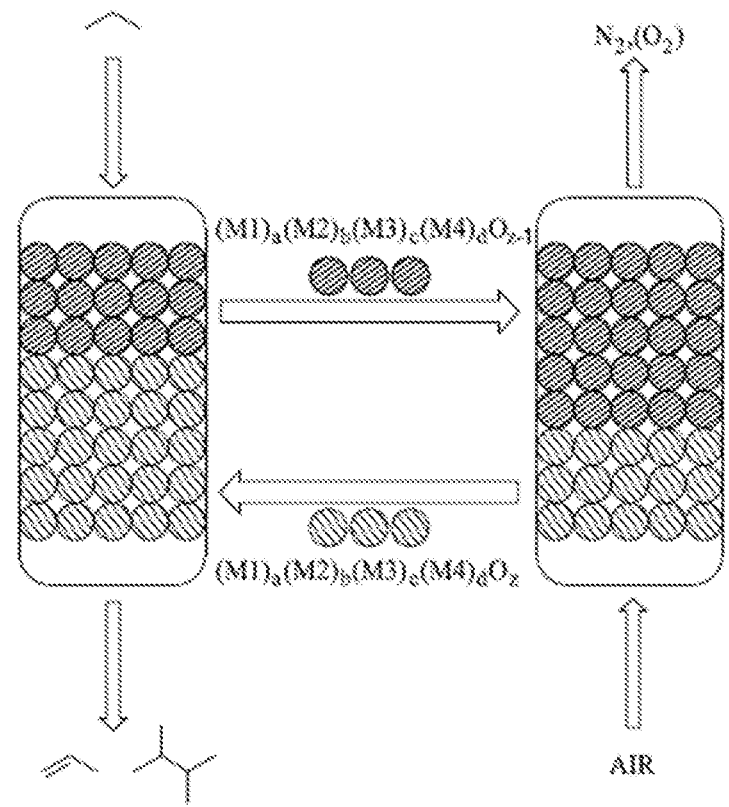
FIG. 4A is a schematic diagram of a process in which a metal oxide is reduced and then oxidized while an n-propane feed is converted to a corresponding propylene and 2,3-dimethyl-butane, according to one embodiment.
Figure 4A:
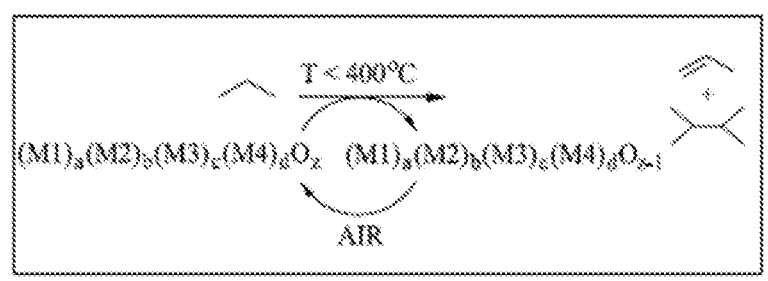
Figure 4B:
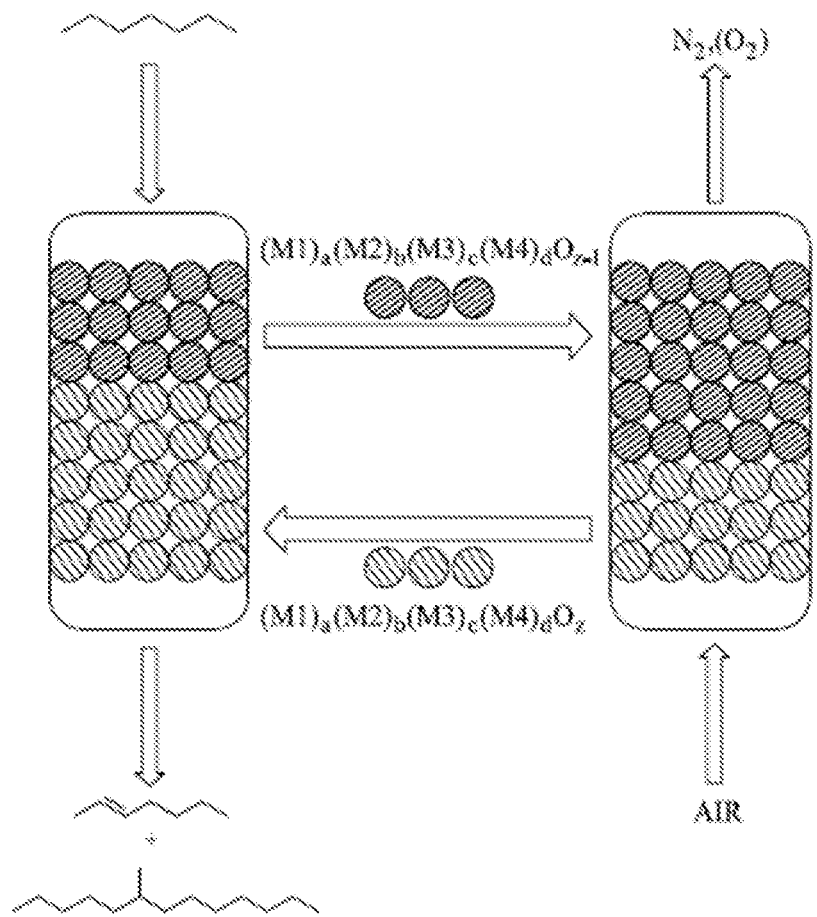
FIG. 4B is a schematic diagram of a process in which a metal oxide is reduced and then oxidized while an n-heptane feed is converted to the corresponding n-heptenes and C14-heavier hydrocarbon products, according to one embodiment.
Figure 4B:
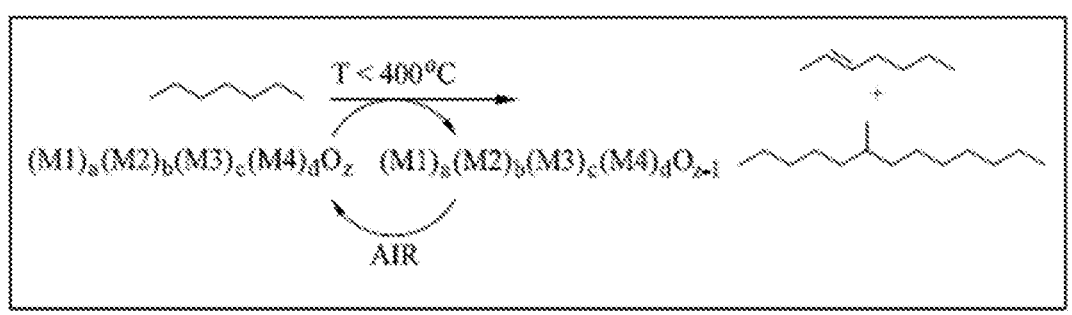

FIGS. 4A and 4B illustrate a schematic diagram of a process in which a metal oxide (M1)a(M2)b(M3)c(M4)dOz is cyclically reduced and then oxidized while the n-propane feed (FIG. 4A), or the n-heptane feed (FIG. 4B), is converted to a corresponding olefin (formed via dehydrogenation) and or heavier hydrocarbon products (formed via dehydrogenative coupling), according to one embodiment. FIG. 4A is a schematic diagram of a process in which a metal oxide is reduced and then oxidized while an n-propane feed is converted to a corresponding propylene and 2,3-dimethylbutane. FIG. 4B is a schematic diagram of a process in which a metal oxide is reduced and then oxidized while an n-heptane feed is converted to the corresponding n-heptenes and C14-heavier hydrocarbon products. The following examples (Examples 1-14) illustrate the embodiments of the present disclosure.

Figure 5A:
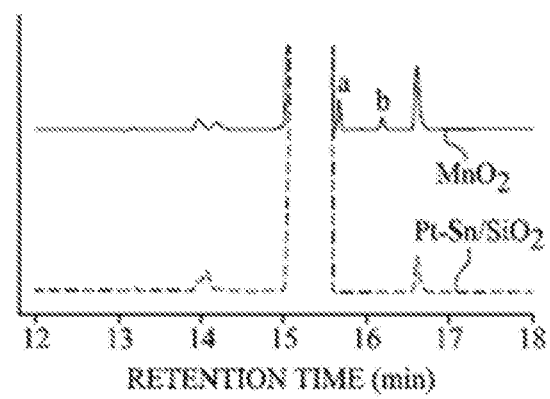
FIG. 5A illustrates gas chromatograms of the products obtained from the reaction of an n-heptane feed using PtSn/SiO2 or MnO2, with an early retention time region where n-heptenes (a and b) elute, according to one embodiment.

Example 1 (Comparative). Attempted dehydrogenation of n-heptane using PtSn/SiO2. In a 300-mL autoclave was loaded 100 g n-heptane and 5 g dehydrogenation catalyst (PtSn/SiO2, 1 wt % Pt, 0.15 wt % Sn). The catalyst was reduced at 250° C. and 500 psig under flowing H2 (100 cm3/min), stirred at 500 rpm for 5 hours. The autoclave was cooled down to room temperature, the overhead gas vented, and the liquid decanted. The autoclave was then recharged with 100 g n-heptane, purged with low pressure of N2, sealed and heated at 250° C. for 24 hours, with stirring (500 rpm). The autoclave was cooled, vented, and the liquid sampled for GC and GC/MS analysis. The reaction did not lead to the formation of the dehydrogenation products (n-heptenes), nor heavier hydrocarbon products (FIG. 5A).

Figure 5B:
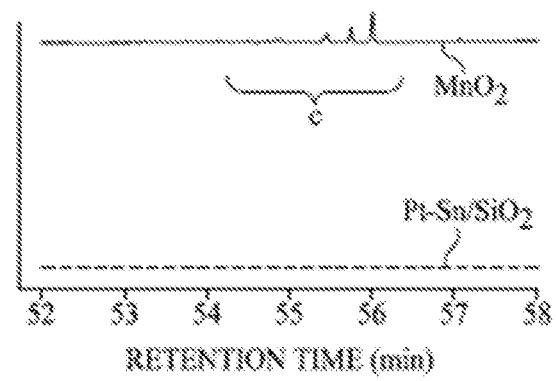
FIG. 5B illustrates gas chromatograms of the products obtained from the reaction of an n-heptane feed using PtSn/SiO2 or MnO2, with a late retention time region where C14-hydrocarbons (c) appear, according to one embodiment.

Example 2. Conversion of n-heptane to n-heptenes and C14-hydrocarbon products using MnO2. In a 300-mL autoclave, was loaded 75 g n-heptane and 15 g MnO2, purged with low pressure of N2, sealed and heated at 250° C. for 24 hours, with stirring (500 rpm). The autoclave was cooled, vented, and the liquid sampled for GC and GC/MS analysis. Formation of the dehydrogenation products (n-heptenes) and heavier hydrocarbon products (C14-products) was observed (FIGS. 5A and 5B). The gas chromatograms of the products obtained from the reaction of an n-heptane feed using MnO2 illustrates an early retention time region where n-heptenes eluted (FIG. 5A, peaks a and b), as well as a late retention time region where C14-hydrocarbon products eluted (FIG. 5B, peak c).

For the following examples (Example 3 (CuO), Example 4 (Ag2O), Example 5 (Na2O2), Example 6 (Ni2O3), Example 7 (BaO2), Example 8 (CuO/SiO2), Example 9 (CuO/Al2O3), Example 10 (Co3O4), Example 11 (Fe2O3), and Example 12 (VOz/Al2O3)), the experiments were performed in 3-mL Swagelok reaction cells. An amount of 0.5 g metal oxide was mixed with 1.5 g of n-heptane in the Swagelok cell, sealed, and heated in an oven at designated temperature and time. The cell was cooled down to room temperature before it was opened to recover the liquid and solid for analysis. The results are summarized in Table 2, with CuO providing higher yields for n-heptenes (0.545 wt %), as compared to the metal oxides of Examples 4-12. A mixture of n-heptenes and C14-hydrocarbon products was observed when using CuO, Na2O2, and BaO2, whereas Ag2O, Ni2O3, CuO/Al2O3, Co3O4, Fe2O3 VOz/Al2O3, led to the direct formation of n-heptenes.

TABLE 2

| Example | 3 | 4 | 5 | 6 | 7 |
|---|---|---|---|---|---|
| Oxides | CuO | Ag2O | Na2O2 | Ni2O3 | BaO2 |
| Temperature, ° C. | 250 | 150 | 275 | 275 | 275 |
| Time, hour | 12 | 8 | 12 | 14 | 12 |
| n-Heptenes in reaction mixture, wt % | 0.545 | 0.155 | 0.046 | 0.154 | 0.033 |
| C14-hydrocarbon products in reaction mixture, wt % | 0.019 | | 0.042 | | 0.023 |

TABLE 2-continued

| Example | 8 | 9 | 10 | 11 | 12 |
|---|---|---|---|---|---|
| Oxides | CuO/SiO2 | CuO/Al2O3 | Co3O4 | Fe2O3 | VOz/Al2O3 |
| Temperature, ° C. | 275 | 275 | 275 | 275 | 250 |
| Time, hour | 20 | 20 | 16 | 16 | 12 |
| n-Heptenes in reaction mixture, wt % | 0.131 | 0.238 | 0.236 | 0.045 | 0.186 |
| C14-hydrocarbon products in reaction mixture, wt % | | | | | |

Figure 6:
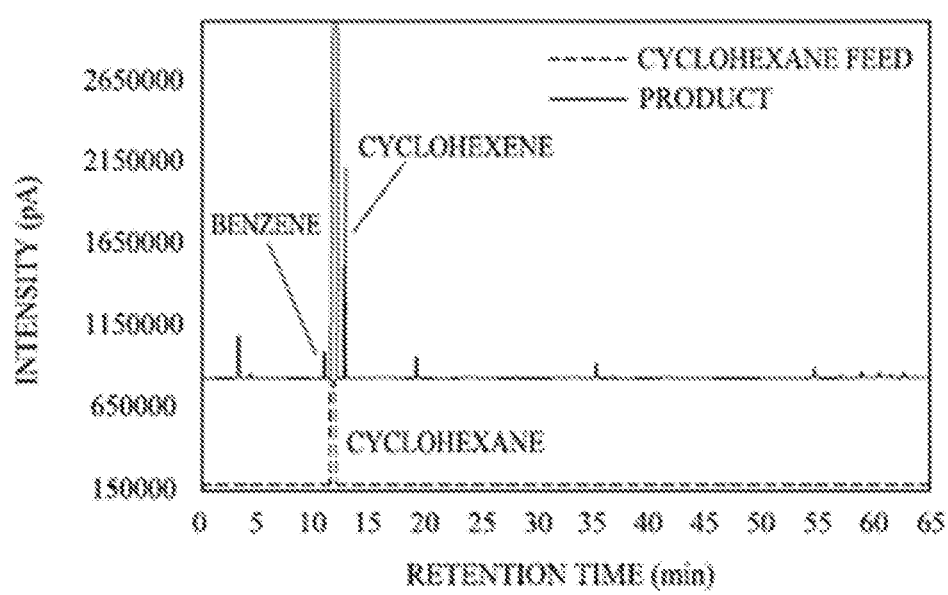
FIG. 6 is a gas chromatogram of a cyclohexane feed and the corresponding dehydrogenation products using CuO, according to one embodiment.

Example 13 (FIG. 6). Dehydrogenation of cyclohexane to cyclohexene using CuO

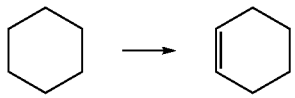 [SMILES: C1CCCCC1 ; C1=CCCCC1]

In an N2-filled glove-box, 0.5 g of CuO and 2.0 g of anhydrous cyclohexane were mixed in a 3 cm3 Swagelok stainless-steel pressure cell. The cell was sealed and placed in an oven held at 275° C. After 3 hours, the cell was taken out and allowed to cool down to room temperature. The cell was then opened and the liquid product recovered and analyzed by gas chromatography (FIG. 6). Example 13 demonstrates that the dehydrogenation of cyclohexane using CuO as an metal oxide, led to the formation of cyclohexene, here obtained as primary product. The GC analysis is shown in FIG. 6. The selectivities to cyclohexene obtained in three identical runs were 74.5%, 76.6%, and 80%.

Figure 7:
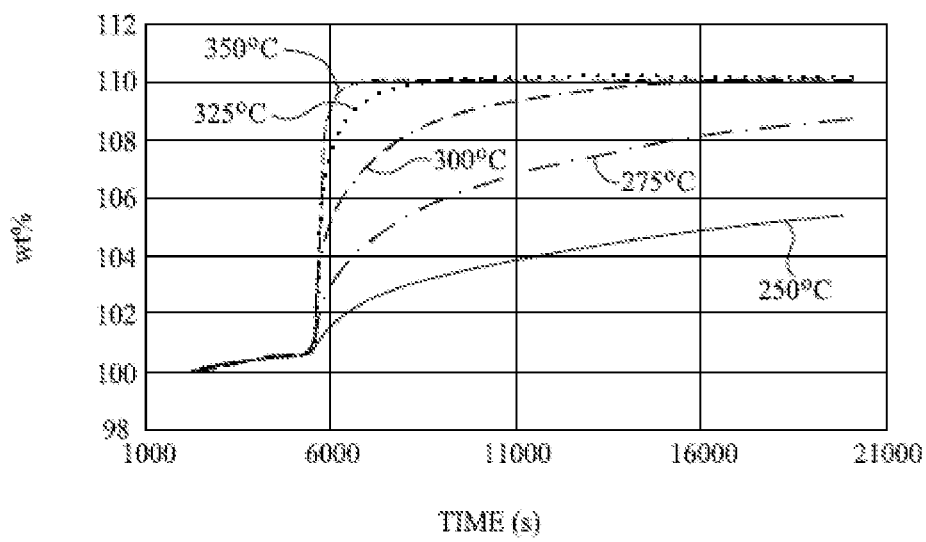
FIG. 7 is a graph illustrating the weight gain (wt %) of CuO as a function of time during an oxidation of the spent (reduced) CuO under flow of air, according to one embodiment.

Example 14. Regeneration of CuO using air. The spent (reduced) metal oxides in the examples above were oxidized under flowing air on a TGA instrument (Mettler-Toledo TGA/SDTA851e). The sample was first dried to a constant weight under flowing helium at 200° C., then the flowing gas was switched to air and the temperature was quickly ramped to the desired value and held for 3 hours. As the spent metal oxide was oxidized, the weight gain was recorded. As the weight gain stopped, the spent metal oxide was fully oxidized. FIG. 7 is a graph illustrating the weight changes during oxidation of the spent CuO under flow of air at various temperatures. For example, after complete regeneration of CuO, a gain of 10 wt % of the oxygen content of the metal oxide was observed at a temperature range of 325° C. to 350° C., within a minute. At 300° C., the CuO was completely regenerated after about 2.5 hours.

Figure 8:
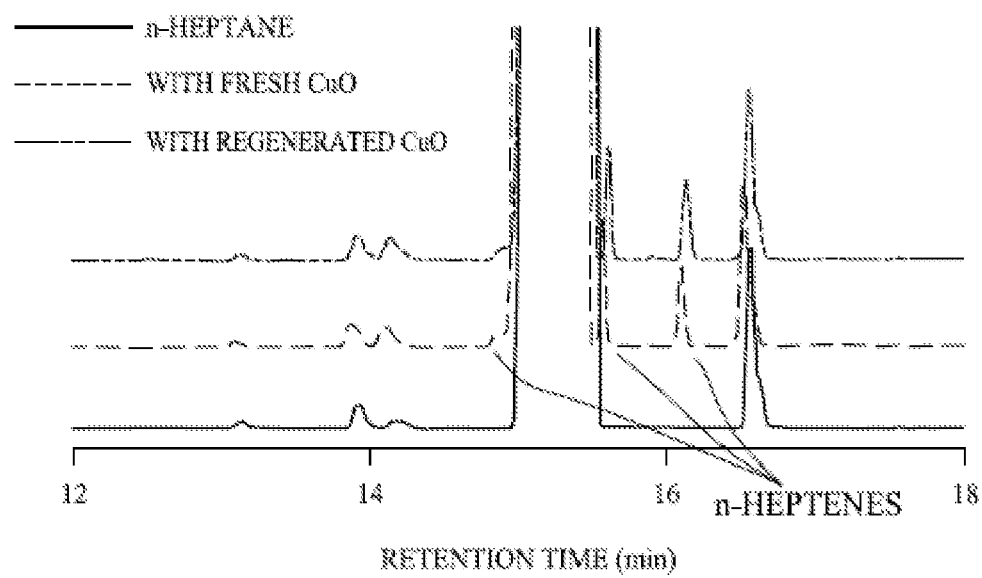
FIG. 8 illustrates gas chromatograms of n-heptane dehydrogenation conversion using fresh CuO and regenerated CuO, according to one embodiment.

Efficacy of the regenerated metal oxide for paraffin conversion was confirmed (FIG. 8). Comparison of GC traces for n-heptane conversion using fresh CuO and regenerated CuO is illustrated in FIG. 8. GC traces for n-heptane conversion show that the regenerated CuO was still active.

Overall, the present disclosure provides processes to convert paraffins to corresponding olefins and or heavier hydrocarbons under mild conditions (e.g., low temperature ≤500° C.) using metal oxides as an oxygen carrier. Processes of the present disclosure can provide the following advantages: 1) reduction of the metal oxides can provide significant driving force to overcome thermodynamic limitations for paraffin conversions to olefins or heavier hydrocarbons, thus the reaction can be performed at significantly lower temperatures (e.g., <400° C.) than conventional approaches (e.g., steam cracking or dehydrogenation), resulting in reduction of greenhouse gas (GHG) emissions; 2) high selectivity for the formation of monoolefins, such as cyclic olefins, can be obtained (such as a selectivity of 50% or greater), thus preventing the formation of aromatics (e.g., benzene); 3) little or no direct contact of O2 with hydrocarbons, thus avoiding undesired reactions of free O2 with radical species that lead to over oxidation and improving selectivity vs. direct oxidation; 4) pure O2 is not needed as the first metal oxide can be regenerated via air oxidation. Olefins generated from a process of the present disclosure can be isolated as chemical intermediates, polymerized (e.g., oligomerized) to chemicals, fluids, or distillate products. Lastly, commercially valuable products, such as ethylene and propylene, can be formed using processes of the present disclosure.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While the present disclosure has been described with respect to a number of embodiments and examples, those skilled in the art, having benefit of this disclosure, will appreciate that other embodiments can be devised which do not depart from the scope and spirit of the present disclosure.

The invention claimed is:

1. A process for upgrading a hydrocarbon feed, comprising:
   introducing at a temperature of from about 50° C. to about 500° C. a hydrocarbon feed comprising paraffins to a composition consisting essentially of a first metal oxide to perform a dehydrogenation and/or a dehydrogenative coupling, the introducing forming a second metal oxide that is a reduced form of the first metal oxide;
   obtaining, from the introducing of the hydrocarbon feed, a product mixture comprising one or more C3-C50 cyclic olefin, one or more C2-C50 acyclic olefin, one or more C5-C200 hydrocarbon, or a mixture thereof, wherein the product mixture comprises less than 500 ppm Hz; and
   introducing an oxidizing agent to the second metal oxide to form the first metal oxide;
   wherein the hydrocarbon feed comprises one or more C3-C50 cyclic alkane and one or more C2-C50 acyclic alkane, and comprises a molar ratio of cyclic alkane to acyclic alkane from about 1:250 to about 250:1; and
   wherein the first metal oxide is represented by Formula (I):

$(M1)_a(M2)_b(M3)_c(M4)_dO_z$ (I)

wherein:
M1 is Mg, Ca, Na, Zn, Cu, Ni, Ba, Ag, Pt, Ti, Zr, Fe, Cr, Co, La, Ce, or Y;
M2 is a group 1, 2, 3, 4, 6, 7, 8, 9, 10, 11, 12, 13, 14, 15, 16, or 17 metal;
M3 is a group 1, 2, 3, 4, 6, 7, 8, 9, 10, 11, 12, 13, 14, 15, 16, or 17 metal;
M4 is a group 1, 2, 3, 4, 6, 7, 8, 9, 10, 11, 12, 13, 14, 15, 16, or 17 metal;
a is 0.01≤a≤4;
b is 0≤b≤4;
c is 0≤c≤4;
d is 0≤d≤4; and
z is 1≤z≤12.

2. The process of claim 1, wherein the oxidizing agent is air.

3. The process of claim 1, wherein introducing the oxidizing agent is performed:
   at a temperature of from about 50° C. to about 1,000° C.;
   at a pressure of from about 15 psig to about 500 psig; and
   at a residence time of about 1 milli-second to about 48 hours.

4. The process of claim 1, wherein the product mixture comprises less than 10 ppm $H_2$.

5. The process of claim 1, wherein the hydrocarbon feed is a naphtha feed.

6. The process of claim 1, wherein the hydrocarbon feed comprises one or more C3-C50 cyclic alkane selected from cyclopropane, cyclobutane, cyclopentane, cyclohexane, cycloheptane, cyclooctane, or mixtures thereof.

7. The process of claim 1, wherein the feed comprises a C2-C50 acyclic alkane selected from propane, n-butane, iso-butane, n-pentane, iso-pentane, neo-pentane, n-hexane, iso-hexane, neo-hexane, n-heptane, iso-heptane, neo-heptane, n-octane, iso-octane, neo-octane, or mixtures thereof.

8. The process of claim 7, wherein the feed comprises a mixture of n-pentane, iso-pentane, cyclo-pentane, and neo-pentane.

9. The process of claim 1, wherein the molar ratio of cyclic alkane to acyclic alkane is from about 1:10 to about 10:1.

10. The process of claim 1, wherein the first metal oxide is selected from $YMnO_4$ or $YMnO_{3.5}$.

11. The process of claim 1, wherein the first metal oxide is selected from CuO, $CuO_2$, $Ag_2O$, $Na_2O_2$, ZnO, $ZnO_2$, NiO, $Ni_2O_3$, $CrO_z$, $FeO_z$, $Fe_2O_3$, $CoO_z$, $Co_2O_3$, $Co_3O_4$, $MnO_z$, $BaO_2$, or $MgO_2$, wherein z is in a range of 1 to 3.5.

12. The process of claim 1, wherein the composition is supported on a support material, and the support material is selected from zeolites, organoclays, $Al_2O_3$, $ZrO_2$, $SiO_2$, $SiO_2/Al_2O_3$, $SiO_2/TiO_2$, silica clay, silicon oxide/clay, or mixtures thereof.

13. The process of claim 1, wherein the first metal oxide has an oxygen capacity of from about 1 wt % to about 50 wt %, based on the weight of the first metal oxide.

14. The process of claim 13, wherein the first metal oxide has an oxygen capacity of from about 3 wt % to about 30 wt % based on the weight of the first metal oxide.

15. The process of claim 1, wherein introducing the hydrocarbon feed to the first metal oxide is performed:
   at a first metal oxide/paraffin molar ratio of from 1,000:1 to 1:1,000 at time zero;
   at a pressure of from about 15 psig to about 2,000 psig; and
   at a residence time of about 1 milli-second to about 48 hours.

16. The process of claim 1, wherein introducing the hydrocarbon feed to the first metal oxide is performed:
   at a first metal oxide/paraffin molar ratio of from 100:1 to 1:100 at time zero;
   at a temperature of about 100° C. to about 350° C.;
   at a pressure of from about 15 psig to about 1,000 psig; and
   at a residence time of about 1 milli-second to about 48 hours.

17. The process of claim 1, wherein introducing the hydrocarbon feed to the first metal oxide is performed:
   at a first metal oxide/paraffin molar ratio of from 10:1 to 1:10 at time zero;
   at a temperature of about 150° C. to about 275° C.;
   at a pressure of from about 15 psig to about 200 psig; and
   at a residence time of about 1 milli-second to about 48 hours.

18. The process of claim 1, wherein the process provides monoolefin products at a selectivity of about 50% or greater.

19. The process of claim 1, wherein the process provides monoolefin products at a selectivity of about 70% or greater.

20. The process of claim 1, wherein the hydrocarbon feed comprises propane and the process provides a C2-C50 acyclic olefin that is propylene.

21. The process of claim 1, wherein the product mixture comprises a di-substituted olefin content in a range of from about 30% to about 80%, based on total unsaturations of the product mixture.

22. The process of claim 1, wherein the product mixture comprises a tri-substituted olefin content in a range of from about 1% to about 50%, based on total unsaturations of the product mixture.

23. The process of claim 1, wherein the composition consists of the first metal oxide.

24. A process for upgrading a hydrocarbon feed, comprising:

introducing at a temperature of from about 50° C. to about 500° C. a hydrocarbon feed comprising paraffins to a first metal oxide to perform a dehydrogenation process and/or a dehydrogenative coupling, the introducing forming a second metal oxide that is a reduced form of the first metal oxide;

obtaining, from the introducing of the hydrocarbon feed, a product mixture comprising one or more C3-C50 cyclic olefin, one or more C2-C50 acyclic olefin, one or more C5-C200 hydrocarbon, or a mixture thereof, wherein the product mixture comprises less than 500 ppm $H_2$; and introducing an oxidizing agent to the second metal oxide to form the first metal oxide;

wherein the hydrocarbon feed comprises one or more C3-C50 cyclic alkane and one or more C2-C50 acyclic alkane, and comprises a molar ratio of cyclic alkane to acyclic alkane from about 1:250 to about 250:1; and wherein the first metal oxide is represented by Formula (I):

$$(M1)_a(M2)_b(M3)_c(M4)_dO_z \qquad (I)$$

wherein:
M1 is Na, Cu, Ni, Ag, Pt, Fe, Co, La, Ce, or Y;
M2 is a group 1, 2, 3, 4, 6, 7, 8, 9, 10, 11, 12, 13, 14, 15, 16, or 17 metal;
M3 is a group 1, 2, 3, 4, 6, 7, 8, 9, 10, 11, 12, 13, 14, 15, 16, or 17 metal;
M4 is a group 1, 2, 3, 4, 6, 7, 8, 9, 10, 11, 12, 13, 14, 15, 16, or 17 metal;
a is 0.01≤a≤4;
b is 0≤b≤4;
c is 0≤c≤4;
d is 0≤d≤4; and
z is 1≤z≤12.

25. A process for upgrading a hydrocarbon feed, comprising:

introducing at a temperature of from about 50° C. to about 500° C. a hydrocarbon feed comprising paraffins to a first metal oxide supported on a support material to perform a dehydrogenation and/or a dehydrogenative coupling, the introducing forming a second metal oxide that is a reduced form of the first metal oxide;

obtaining, from the introducing of the hydrocarbon feed, a product mixture comprising one or more C3-C50 cyclic olefin, one or more C2-C50 acyclic olefin, one or more C5-C200 hydrocarbon, or a mixture thereof, wherein the product mixture comprises less than 500 ppm $H_2$; and introducing an oxidizing agent to the second metal oxide to form the first metal oxide;

wherein the hydrocarbon feed comprises one or more C3-C50 cyclic alkane and one or more C2-C50 acyclic alkane, and comprises a molar ratio of cyclic alkane to acyclic alkane from about 1:250 to about 250:1; and wherein the first metal oxide is represented by Formula (I):

$$(M1)_a(M2)_b(M3)_c(M4)_dO_z \qquad (I)$$

wherein:
M1 is Mg, Ca, Na, Zn, Cu, Ni, Ba, Ag, Pt, Ti, Zr, Fe, Cr, Co, La, Ce, or Y;
M2 is a group 1, 2, 3, 4, 6, 7, 8, 9, 10, 11, 12, 13, 14, 15, 16, or 17 metal;
M3 is a group 1, 2, 3, 4, 6, 7, 8, 9, 10, 11, 12, 13, 14, 15, 16, or 17 metal;
M4 is a group 1, 2, 3, 4, 6, 7, 8, 9, 10, 11, 12, 13, 14, 15, 16, or 17 metal;
a is 0.01≤a≤4;
b is 0≤b≤4;
c is 0≤c≤4;
d is 0≤d≤4; and
z is 1≤z≤12.

* * * * *